United States Patent
Chen et al.

(10) Patent No.: US 11,155,794 B2
(45) Date of Patent: Oct. 26, 2021

(54) METHOD OF PURIFYING A HETEROLOGOUS PROTEIN FROM AN EGG WHITE

(71) Applicant: ALEXION PHARMACEUTICALS, INC., Boston, MA (US)

(72) Inventors: Liang Chen, San Diego, CA (US); Markley C. Leavitt, Lexington, MA (US); Michael Titus, Lexington, MA (US); Stephen Palmieri, Foxboro, MA (US)

(73) Assignee: ALEXION PHARMACEUTICALS, INC., Boston, MA (US)

( * ) Notice: Subject to any disclaimer, the term of this patent is extended or adjusted under 35 U.S.C. 154(b) by 214 days.

(21) Appl. No.: 16/308,137

(22) PCT Filed: Aug. 22, 2017

(86) PCT No.: PCT/US2017/047903
§ 371 (c)(1),
(2) Date: Dec. 7, 2018

(87) PCT Pub. No.: WO2018/039163
PCT Pub. Date: Mar. 1, 2018

(65) Prior Publication Data
US 2019/0177708 A1    Jun. 13, 2019

Related U.S. Application Data

(60) Provisional application No. 62/378,441, filed on Aug. 23, 2016.

(51) Int. Cl.
*C12N 9/20* (2006.01)
*C07K 1/20* (2006.01)
(Continued)

(52) U.S. Cl.
CPC ........... *C12N 9/20* (2013.01); *B01D 15/1871* (2013.01); *B01D 15/24* (2013.01); *B01D 15/327* (2013.01);
(Continued)

(58) Field of Classification Search
None
See application file for complete search history.

(56) References Cited

U.S. PATENT DOCUMENTS

2008/0071067 A1    3/2008  Chen et al.
2015/0064769 A1*   3/2015  Xenopoulos ............ C07K 1/36
                                                     435/238

FOREIGN PATENT DOCUMENTS

WO    WO 2011/133960      * 10/2011
WO    WO 2011/133960 A2     10/2011
WO    WO 2015/164320 A1     10/2015

OTHER PUBLICATIONS

Sheridan et al., "FDA approves 'farmaceutical' drug from transgenic chickens," Nature Biotechnology 34(2): 117-119 (2016), published Feb. 2, 2016.
(Continued)

*Primary Examiner* — Erin M. Bowers
(74) *Attorney, Agent, or Firm* — Medler Ferro Woodhouse & Mills

(57) ABSTRACT

The present invention is related a method of purifying a heterologous protein from an egg white. In some embodiments, the disclosure is directed to a method of purifying a heterologous protein from an egg white comprising the heterologous protein, the method comprising, (a) adjusting the pH of the egg white to a pH of 5.8 to 6.5 to form a pH-adjusted egg white; (b) filtering the pH-adjusted egg white of (a) and collecting a first filtrate; (c) subjecting the first filtrate of (b) to a hydrophobic interaction chromatography matrix, and collecting a first eluate comprising the
(Continued)

heterologous protein; (d) adjusting the pH of the first eluate of (c) to a pH of 5.0 to 5.6 to form a pH-adjusted eluate; (e) filtering the pH-adjusted eluate to obtain a second filtrate; (f) adjusting the pH of the second filtrate to a pH of 3.0 to 4.0 to form a pH-adjusted second filtrate; (g) neutralizing the pH-adjusted second filtrate of (f) to a pH of 5.0 to 8.0 to form a neutralized solution; (h) subjecting the neutralized solution to a cation exchange chromatography matrix and collecting a second eluate comprising the heterologous protein.

47 Claims, 12 Drawing Sheets

Specification includes a Sequence Listing.

(51) Int. Cl.
| | | |
|---|---|---|
| *C07K 1/34* | (2006.01) | |
| *C07K 1/36* | (2006.01) | |
| *B01D 15/18* | (2006.01) | |
| *B01D 15/24* | (2006.01) | |
| *B01D 15/32* | (2006.01) | |
| *B01D 15/36* | (2006.01) | |
| *B01D 61/14* | (2006.01) | |
| *C07K 1/18* | (2006.01) | |

(52) U.S. Cl.
CPC ......... *B01D 15/362* (2013.01); *B01D 61/145* (2013.01); *C07K 1/18* (2013.01); *C07K 1/20* (2013.01); *C07K 1/34* (2013.01); *C07K 1/36* (2013.01); *B01D 2311/18* (2013.01); *B01D 2311/2626* (2013.01); *B01D 2315/16* (2013.01)

(56) References Cited

OTHER PUBLICATIONS

International Search Report and Written Opinion issued in PCT/US2017/047903, dated Nov. 9, 2017.

* cited by examiner

SEQ ID NO: 1

```
Ser Gly Gly Lys Leu Thr Ala Val Asp Pro Glu Thr Asn Met Asn Val
1               5                   10                  15
Ser Glu Ile Ile Ser Tyr Trp Gly Phe Pro Ser Glu Glu Tyr Leu Val
                20                  25                  30
Glu Thr Glu Asp Gly Tyr Ile Leu Cys Leu Asn Arg Ile Pro His Gly
            35                  40                  45
Arg Lys Asn His Ser Asp Lys Gly Pro Lys Pro Val Val Phe Leu Gln
        50                  55                  60
His Gly Leu Leu Ala Asp Ser Ser Asn Trp Val Thr Asn Leu Ala Asn
65                  70                  75                  80
Ser Ser Leu Gly Phe Ile Leu Ala Asp Ala Gly Phe Asp Val Trp Met
                85                  90                  95
Gly Asn Ser Arg Gly Asn Thr Trp Ser Arg Lys His Lys Thr Leu Ser
                100                 105                 110
Val Ser Gln Asp Glu Phe Trp Ala Phe Ser Tyr Asp Glu Met Ala Lys
            115                 120                 125
Tyr Asp Leu Pro Ala Ser Ile Asn Phe Ile Leu Asn Lys Thr Gly Gln
        130                 135                 140
Glu Gln Val Tyr Val Gly His Ser Gln Gly Thr Thr Ile Gly Phe
145                 150                 155                 160
Ile Ala Phe Ser Gln Ile Pro Glu Leu Ala Lys Arg Ile Lys Met Phe
                165                 170                 175
Phe Ala Leu Gly Pro Val Ala Ser Val Ala Phe Cys Thr Ser Pro Met
            180                 185                 190
Ala Lys Leu Gly Arg Leu Pro Asp His Leu Ile Lys Asp Leu Phe Gly
        195                 200                 205
Asp Lys Glu Phe Leu Pro Gln Ser Ala Phe Leu Lys Trp Leu Gly Thr
    210                 215                 220
His Val Cys Thr His Val Ile Leu Lys Glu Leu Cys Gly Asn Leu Cys
225                 230                 235                 240
Phe Leu Leu Cys Gly Phe Asn Glu Arg Asn Leu Asn Met Ser Arg Val
                245                 250                 255
Asp Val Tyr Thr Thr His Ser Pro Ala Gly Thr Ser Val Gln Asn Met
            260                 265                 270
Leu His Trp Ser Gln Ala Val Lys Phe Gln Lys Phe Gln Ala Phe Asp
        275                 280                 285
Trp Gly Ser Ser Ala Lys Asn Tyr Phe His Tyr Asn Gln Ser Tyr Pro
    290                 295                 300
Pro Thr Tyr Asn Val Lys Asp Met Leu Val Pro Thr Ala Val Trp Ser
305                 310                 315                 320
Gly Gly His Asp Trp Leu Ala Asp Val Tyr Asp Val Asn Ile Leu Leu
                325                 330                 335
Thr Gln Ile Thr Asn Leu Val Phe His Glu Ser Ile Pro Glu Trp Glu
            340                 345                 350
His Leu Asp Phe Ile Trp Gly Leu Asp Ala Pro Trp Arg Leu Tyr Asn
        355                 360                 365
Lys Ile Ile Asn Leu Met Arg Lys Tyr Gln
370                 375
```

FIG.12

SEQUENCE LISTING

```
<160> NUMBER OF SEQ ID NOS: 1

<210> SEQ ID NO 1
<211> LENGTH: 378
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 1

Ser Gly Gly Lys Leu Thr Ala Val Asp Pro Glu Thr Asn Met Asn Val
1               5                   10                  15

Ser Glu Ile Ile Ser Tyr Trp Gly Phe Pro Ser Glu Glu Tyr Leu Val
            20                  25                  30

Glu Thr Glu Asp Gly Tyr Ile Leu Cys Leu Asn Arg Ile Pro His Gly
        35                  40                  45

Arg Lys Asn His Ser Asp Lys Gly Pro Lys Pro Val Val Phe Leu Gln
    50                  55                  60

His Gly Leu Leu Ala Asp Ser Ser Asn Trp Val Thr Asn Leu Ala Asn
65                  70                  75                  80

Ser Ser Leu Gly Phe Ile Leu Ala Asp Ala Gly Phe Asp Val Trp Met
                85                  90                  95

Gly Asn Ser Arg Gly Asn Thr Trp Ser Arg Lys His Lys Thr Leu Ser
            100                 105                 110

Val Ser Gln Asp Glu Phe Trp Ala Phe Ser Tyr Asp Glu Met Ala Lys
        115                 120                 125

Tyr Asp Leu Pro Ala Ser Ile Asn Phe Ile Leu Asn Lys Thr Gly Gln
    130                 135                 140

Glu Gln Val Tyr Tyr Val Gly His Ser Gln Gly Thr Thr Ile Gly Phe
145                 150                 155                 160

Ile Ala Phe Ser Gln Ile Pro Glu Leu Ala Lys Arg Ile Lys Met Phe
                165                 170                 175

Phe Ala Leu Gly Pro Val Ala Ser Val Ala Phe Cys Thr Ser Pro Met
            180                 185                 190

Ala Lys Leu Gly Arg Leu Pro Asp His Leu Ile Lys Asp Leu Phe Gly
        195                 200                 205

Asp Lys Glu Phe Leu Pro Gln Ser Ala Phe Leu Lys Trp Leu Gly Thr
    210                 215                 220

His Val Cys Thr His Val Ile Leu Lys Glu Leu Cys Gly Asn Leu Cys
225                 230                 235                 240

Phe Leu Leu Cys Gly Phe Asn Glu Arg Asn Leu Asn Met Ser Arg Val
                245                 250                 255

Asp Val Tyr Thr Thr His Ser Pro Ala Gly Thr Ser Val Gln Asn Met
            260                 265                 270

Leu His Trp Ser Gln Ala Val Lys Phe Gln Lys Phe Gln Ala Phe Asp
        275                 280                 285

Trp Gly Ser Ser Ala Lys Asn Tyr Phe His Tyr Asn Gln Ser Tyr Pro
    290                 295                 300

Pro Thr Tyr Asn Val Lys Asp Met Leu Val Pro Thr Ala Val Trp Ser
305                 310                 315                 320

Gly Gly His Asp Trp Leu Ala Asp Val Tyr Asp Val Asn Ile Leu Leu
                325                 330                 335

Thr Gln Ile Thr Asn Leu Val Phe His Glu Ser Ile Pro Glu Trp Glu
            340                 345                 350

His Leu Asp Phe Ile Trp Gly Leu Asp Ala Pro Trp Arg Leu Tyr Asn
        355                 360                 365

Lys Ile Ile Asn Leu Met Arg Lys Tyr Gln
    370                 375
```

METHOD OF PURIFYING A HETEROLOGOUS PROTEIN FROM AN EGG WHITE

SEQUENCE LISTING

The instant application contains a Sequence Listing which has been submitted electronically in ASCII format and is hereby incorporated by reference in its entirety. Said ASCII copy, created on Aug. 16, 2017, is named 0054-0001WO1_SL.txt and is 3,671 bytes in size.

FIELD OF THE INVENTION

The present invention is related a method of purifying a heterologous protein from an egg white. In some embodiments, the disclosure is directed to a method of purifying a heterologous protein from an egg white comprising the heterologous protein, the method comprising, (a) adjusting the pH of the egg white to a pH of 5.8 to 6.5 to form a pH-adjusted egg white; (b) filtering the pH-adjusted egg white of (a) and collecting a first filtrate; (c) subjecting the first filtrate of (b) to a hydrophobic interaction chromatography matrix, and collecting a first eluate comprising the heterologous protein; (d) adjusting the pH of the first eluate of (c) to a pH of 5.0 to 5.6 to form a pH-adjusted eluate; (e) filtering the pH-adjusted eluate to obtain a second filtrate; (f) adjusting the pH of the second filtrate to a pH of 3.0 to 4.0 to form a pH-adjusted second filtrate; (g) neutralizing the pH-adjusted second filtrate of (f) to a pH of 5.0 to 8.0 to form a neutralized solution; (h) subjecting the neutralized solution to a cation exchange chromatography matrix and collecting a second eluate comprising the heterologous protein.

BACKGROUND OF THE INVENTION

Transgenic avians (e.g., transgenic chickens, quails or turkeys) are a desirable expression system for obtaining heterologous proteins for use in pharmaceutical or other commercial applications that require large amounts of protein supply. A hen can lay up to 330 eggs per year, each containing 6.5 grams of protein. About 3.5 grams of the total protein is from egg white, of which 90% is accounted for by seven different proteins; the ovalbumin alone accounts for 2 grams of egg white protein (about 50% of the egg white protein). Currently, the average heterologous protein derived from oviduct specific expression of a transgene and recovered from the egg white is known to be about 5-10 mg per egg. Advantages of heterologous protein production in chicken eggs include short generation times and prolific rates of reproduction via artificial insemination. Various proteins have been expressed in eggs of transgenic chickens. See, e.g., U.S. Pat. No. 6,730,822 and U.S. Publication No. 2006/0015960.

Many heterologous therapeutic proteins (e.g., recombinant human proteins such as cytokines (e.g., erythropoietin, granulocyte colony-stimulating factor (GC-SF), interferons, and granulocyte-macrophage colony-stimulating factor (GM-CSF)), antibodies, and various human lysosomal enzymes) are of interest to the pharmaceutical industry. The therapeutic proteins can readily be obtained in significant quantities from, for example, egg white of transgenic chickens. Traditional methods of isolating heterologous proteins from the egg white, however, often rely on use of immunoaffinity procedures or other procedures only suitable for small scale production (e.g., involving total egg white volume of 5 L at most). For a large-scale protein production, such a procedure is not practical based on costs, labor, and time.

BRIEF SUMMARY OF THE INVENTION

Provided herein are methods of purifying a heterologous protein from an egg white using the methods disclosed herein. In some embodiments, the disclosure is directed to a method of purifying a heterologous protein from an egg white comprising the heterologous protein, the method comprising, (a) adjusting the pH of the egg white to a pH of 5.8 to 6.5 to form a pH-adjusted egg white; (b) filtering the pH-adjusted egg white of (a) and collecting a first filtrate; (c) subjecting the first filtrate of (b) to a hydrophobic interaction chromatography matrix, and collecting a first eluate comprising the heterologous protein; (d) adjusting the pH of the first eluate of (c) to a pH of 5.0 to 5.6 to form a pH-adjusted eluate; (e) filtering the pH-adjusted eluate to obtain a second filtrate; (f) adjusting the pH of the second filtrate to a pH of 3.0 to 4.0 to form a pH-adjusted second filtrate; (g) neutralizing the pH-adjusted second filtrate of (f) to a pH of 5.0 to 8.0 to form a neutralized solution; (h) subjecting the neutralized solution to a cation exchange chromatography matrix and collecting a second eluate comprising the heterologous protein.

In some embodiments, the method further comprises (i) subjecting the second eluate to nanofiltration to form a third filtrate. In some embodiments, the method further comprises (j) subjecting the third filtrate to an anion exchange chromatography matrix and collecting a third eluate comprising the heterologous protein. In some embodiments, the method further comprises (k) subjecting the third eluate to a second hydrophobic interaction chromatography matrix, and collecting a fourth eluate comprising the heterologous protein. In some embodiments, the method further comprises (l) subjecting the fourth eluate to ultrafiltration/diafiltration (UF/DF).

Various proteins can be purified according to the present disclosure. In some embodiments, the heterologous protein is a therapeutic protein. In some embodiments, the therapeutic protein is sebelipase alfa.

In some embodiments, the egg white of the disclosure is a pooled egg white with a volume of greater than 1 liter. In some embodiments, the egg white is a pooled egg white with a volume of greater than 10 liters. In some embodiments, the egg white is a pooled egg white with a volume of greater than 50 liters.

The pH of the egg white of the process of (a) can be adjusted. In some embodiments, the pH of (a) is between 5.9 and 6.2. In some embodiments, the pH of (a) is adjusted using an acidic buffer. In some embodiments, the pH of (a) is adjusted using an acidic buffer comprising an acidic agent selected from the group consisting of acetic acid, hydrochloric acid, sulfuric acid, nitric acid, phosphoric acid, hydrofluoric acid, hydrobromic acid, perchloric acid, citric acid, boric acid, tartaric acid, lactic acid, formic acid, oxalic acid, uric acid, and barbituric acid. In some embodiments, the acidic buffer comprises about 5M to about 6M of an acetate salt. In some embodiments, the acidic buffer comprises about 5M to about 6M sodium acetate.

In some embodiments, the acidic buffer is from about 0.5 wt % to about 2 wt % per kilogram of the egg white. In some embodiments, the pH of the acidic buffer is about 4.0 to about 6.5.

The buffer can be added to the egg white at various rates. In some embodiments, the acidic buffer is added to the egg white of (a) at a rate of at least about 1% (vol/vol) per minute. In some embodiments, the egg white is stirred concurrently while the pH is adjusted.

In some embodiments, the egg white is stirred concurrently while the pH is adjusted. In some embodiments, the egg white of (a) is about 2° C. to about 25° C. In some embodiments, the conductivity of the pH-adjusted egg white is about 8 mS/cm to about 20 mS/cm. In some embodiments, the method comprises allowing the pH-adjusted egg white to settle such that the egg white separates into top, middle and bottom layers. In some embodiments, the method comprises a step of isolating the middle layer, and subjecting the isolated middle layer to the filtering in (b).

In some embodiments, the method comprises filtering the pH-adjusted egg white. In some embodiments, the filtering of (b) comprises passing the pH-adjusted egg white through a filter having an average pore size ranging from about 0.1 µm to about 100 µm. In some embodiments, the filtering of (b) comprises passing the pH-adjusted egg white through a plurality of filters. In some embodiments, the filter comprises an area of at least about 2 m$^2$. In some embodiments, the filter comprises an area of at least about 8 m$^2$. In some embodiments, the egg white is passed through the filter under a differential pressure less than about 30 psi. In some embodiments, the egg white is passed through the filter under a differential pressure less than about 15 psi.

In some embodiments, the first filtrate is warmed to room temperature. In some embodiments, the hydrophobic interaction chromatography matrix of (c) is a phenyl, octyl, or butyl hydrophobic interaction chromatography matrix. In some embodiments, the hydrophobic interaction chromatography matrix of (c) is a phenyl hydrophobic interaction chromatography matrix.

In some embodiments, the heterologous protein is eluted from the hydrophobic interaction chromatography matrix by a decreasing salt gradient.

In some embodiments, the adjusting the pH of (d) is adjusted using an acidic buffer comprising an acidic agent selected from the group consisting of acetic acid, hydrochloric acid, sulfuric acid, nitric acid, phosphoric acid, hydrofluoric acid, hydrobromic acid, perchloric acid, citric acid, boric acid, tartaric acid, lactic acid, formic acid, oxalic acid, uric acid, and barbituric acid. In some embodiments, the pH of (d) is adjusted to a pH of 5.2 to 5.5

In some embodiments, the filtering of (e) comprises passing the eluted heterologous protein through a filter having an average pore size ranging from about 0.1 µm to about 10 µm. In some embodiments, the filtering of (e) comprises passing the eluted heterologous protein through a filter having an average pore size ranging from about 0.5 µm to about 5 µm.

In some embodiments, the pH of the second filtrate is adjusted using an acidic buffer comprising an acidic agent selected from the group consisting of acetic acid, hydrochloric acid, sulfuric acid, nitric acid, phosphoric acid, hydrofluoric acid, hydrobromic acid, perchloric acid, citric acid, boric acid, tartaric acid, lactic acid, formic acid, oxalic acid, uric acid, and barbituric acid. In some embodiments, the pH of the second filtrate is adjusted to a pH of 3.5 to 3.9. In some embodiments, the pH of the pH-adjusted second filtrate is maintained for 10 minutes to 40 minutes. In some embodiments, pH-adjusted second filtrate is neutralized according to (g) using a basic buffer comprising a basic agent selected from the group consisting of an amine, an ammonia, a carbonate, a bicarbonate, a borate, and a phosphate.

In some embodiments, the cation exchange chromatography matrix is selected from a matrix comprising a methyl sulfonate group, diethylaminoethyl group or an ammonium group. In some embodiments, the heterologous protein is eluted using an increasing salt gradient.

In some embodiments, the nanofiltration of (i) comprises passing the second eluate through a filter having an average pore size from about 0.05 µm to about 0.2 µm. In some embodiments, the nanofiltration of (i) comprises passing the second eluate through multiple nanofilters.

In some embodiments, the anion exchange chromatography matrix is selected from a matrix comprising a quaternary ammonium diethylaminoaminoethyl (DEAE) group and diethylaminoethyl group.

In some embodiments, the second hydrophobic interaction chromatography matrix is different from the hydrophobic interaction chromatography matrix of (c). In some embodiments, the second hydrophobic interaction chromatography matrix is a butyl-hydrophobic interaction chromatography matrix.

In some embodiments, the ultrafiltration/diafiltration comprises passing the third eluate through a filter having an average pore size from about 0.02 µm to about 0.4 µm, or about 0.05 µm to about 0.4 µm. In some embodiments, ultrafiltration/diafiltration results in the concentration of the heterologous protein to about 0.5 mg/ml to about 5 mg/ml. In some embodiments, the ultrafiltration/diafiltration comprises use of a citrate buffer.

In some embodiments, the disclosure is directed to a method of purifying a heterologous protein from an egg white comprising the heterologous protein, the method comprising; (a) adjusting the pH of the egg white to a pH of 5.8 to 6.5 to form a pH-adjusted egg white; (b) filtering the pH-adjusted egg white of (a) and collecting a first filtrate; (c) subjecting the supernatant of (b) to a hydrophobic interaction chromatography matrix, and collecting an eluate comprising the heterologous protein; (d) filtering the eluate to obtain a second filtrate; (e) adjusting the pH of the second filtrate to a pH of 3.0 to 4.0 to form a pH-adjusted second filtrate; (f) neutralizing the pH-adjusted second filtrate of (e) to a pH of 5.0 to 8.0 to form a neutralized solution; (g) subjecting the neutralized solution of (f) to a cation exchange chromatography matrix and collecting a second eluate comprising the heterologous protein; (h) subjecting the second eluate of (g) to nanofiltration to form a third filtrate comprising the heterologous protein; (i) subjecting the third filtrate to an anion exchange chromatography matrix and collecting a third eluate comprising the heterologous protein; (j) subjecting the third eluate to a second hydrophobic interaction chromatography matrix, and collecting a fourth eluate comprising the heterologous protein; and (k) subjecting the fourth eluate to ultrafiltration/diafiltration (UF/DF). In some embodiments, the heterologous protein is a therapeutic protein. In some embodiments, the therapeutic protein is sebelipase alfa.

In some embodiments, the disclosure is directed to a method of purifying a heterologous protein from an egg white comprising the heterologous protein, the method comprising; (a) adjusting the pH of the egg white to a pH of 5.8 to 6.5 to form a pH-adjusted egg white; (b) filtering the pH-adjusted egg white of (a) and collecting a first filtrate; (c) subjecting the first filtrate of (b) to a hydrophobic interaction chromatography matrix, and collecting a first eluate comprising the heterologous protein; (d) adjusting the pH of the elution to a pH of 3.0 to 4.0 to form a pH-adjusted eluate comprising the heterologous protein; (e) neutralizing the pH-adjusted eluate of (d) to a pH of 5.0 to 8.0 to form a neutralized solution comprising the heterologous protein; (f) subjecting the neutralized solution to a cation exchange chromatography matrix and collecting a second eluate comprising the heterologous protein.

In some embodiments, the method further comprises (g) subjecting the second eluate to nanofiltration to form a third filtrate comprising the heterologous protein. In some embodiments, the method further comprises (h) subjecting the third filtrate to an anion exchange chromatography matrix and collecting a third eluate. In some embodiments, the method further comprises (i) subjecting the eluate to a second hydrophobic interaction chromatography matrix and collecting a fourth eluate comprising the heterologous protein. In some embodiments, the method further comprises (j) subjecting the fourth eluate to ultrafiltration/diafiltration (UF/DF).

In some embodiments, the method is directed to a product made by the process described herein.

BRIEF DESCRIPTION OF DRAWINGS

The foregoing and other features and aspects of the present technology can be better understood from the following description of embodiments and as illustrated in the accompanying drawings. The accompanying drawings, which are incorporated herein and form a part of the specification, further serve to illustrate the principles of the present technology.

FIG. 12: Sequence of full-length sebelipase alfa (SEQ ID NO. 1).

DETAILED DESCRIPTION OF THE INVENTION

Figure 1:
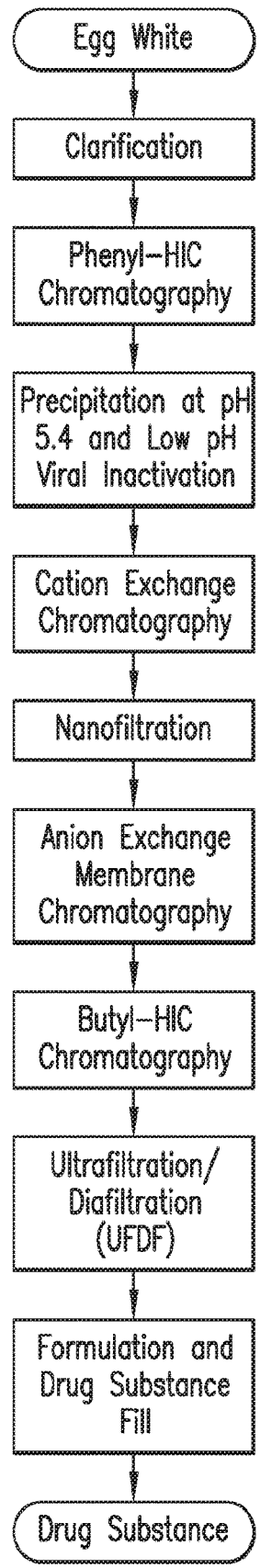
FIG. 1: Schematic overview of a purification process of a heterologous protein, sebelipase alfa.

It should be appreciated that the particular implementations shown and described herein are examples and are not intended to otherwise limit the scope of the application in any way.

The published patents, patent applications, websites, company names, and scientific literature referred to herein are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Technical and scientific terms used herein have the meaning commonly understood by one of skill in the art to which the present application pertains, unless otherwise defined. Reference is made herein to various methodologies and materials known to those of skill in the art. The disclosures of any documents cited herein is incorporated by reference herein in their entireties.

The term "purifying" means a method or step performed to isolate a heterologous protein from one or more other impurities or components present in an egg white. The components being separated include other proteins, aggregates of the desired heterologous protein, DNA, RNA, endotoxins, and viruses present in the egg white A purifying step can be performed using a resin, membrane, or any other solid support that binds either the desired heterologous protein or contaminants (such as through the use of affinity chromatography, hydrophobic interaction chromatography, anion or cation exchange chromatography, mixed-mode chromatography resin, or molecular sieve chromatography). A heterologous protein can be purified from a solution including the heterologous protein using at least one chromatography column and/or chromatographic membrane (such as any of the chromatography columns described herein).

This disclosure relates to efficient methods of purifying a heterologous protein from egg white (e.g., obtained from eggs laid by transgenic chickens). The methods disclosed are particularly useful for bulk chromatographic isolation of heterologous proteins (e.g., recombinant proteins) from the egg white. The methods disclosed provide a homogeneous, low viscosity egg white solution followed by subsequent processes that efficiently isolate the desired heterologous protein. The process is especially suitable for processing a therapeutic heterologous protein from egg whites.

pH Adjustments During Purification

While the skilled artisan will know that some pH adjustments are commonly used during protein purifications, the present disclosure discloses that specific pH adjustments during specific processes are especially advantageous when purifying a heterologous protein from egg whites, especially when larger volumes of egg whites are used.

In some embodiments, the disclosure of the present invention has found that adjusting the pH during various specific processes throughout the purification process for egg whites can allow for an increased volume of egg whites to be processed, and an increased amount of heterologous protein to be purified. In some embodiments, the disclosure of the present invention has found that adjusting the pH during various purification processes can allow for increased efficiency, reduced costs, and/or reduced time of purification of the desired heterologous protein. The pH adjustments described herein can accomplish one or more beneficial aspects of the purification process. For example, in some embodiments, the pH can be adjusted during clarification to render the pooled egg whites less viscous, the pH of the first eluate can be adjusted after the hydrophobic column to precipitate protein impurities, the pH of the of second filtrate can be adjusted to remove impurities and to inactivate viruses, and the pH of the pH-adjusted second filtrate can be neutralized in order to prepare the filtrate to be subjected to a chromatography matrix, e.g., a cation exchange matrix.

In some embodiments, the pH is adjusted during four processes during the purification process: (1) adjusting the pH to the egg-whites to form a pH-adjusted egg white; (2) adjusting the pH of a first eluate, to form a pH-adjusted first eluate; (3) adjusting the pH of a second filtrate, to form a pH-adjusted second filtrate; and (4) neutralizing the pH of the second filtrate, to form a neutralized solution.

In some embodiments, the pH of the pH-adjusted egg white is a value such that the pH-adjusted egg white is rendered less viscous. For example, the mixed pooled egg white in the clarification step can have a pH at least about 5 (e.g., at least about 5.2, at least about 5.4, at least about 5.6, at least about 5.7, at least about 5.8 or at least about 5.9) and/or at most about 6.5 (e.g., at most about 6.3, at most about 6.2 or at most about 6.1). In some embodiments, the pH-adjusted egg white can have a pH of 5.8 to 6.5. In some embodiments, the pH-adjusted egg white can have a pH of 5.9 to 6.2. In some embodiments, the pH-adjusted egg white can have a pH of about 6. Without wishing to be bound by theory, it is believed that such a pH (e.g., about 6) can allow formation of the largest amount of precipitates from egg white that settle under gravity, thereby reducing the need for filtration and facilitating formation of a homogeneous, low viscosity egg white solution. In some embodiments, the pH is maintained throughout the clarification process, i.e., the pH is maintained until the egg whites are subjected to a hydrophobic interaction chromatography matrix. In some embodiments, the pH off the pooled egg whites is maintained until the egg whites are filtered. In some embodiments, the pH off the pooled egg whites is maintained until the precipitation of the impurities is sufficiently accomplished.

In some embodiments, the pH of the first eluate is a value such that protein impurities are precipitated out before the viral inactivation process. For example, the pH of the first eluate can have a pH at least about 5 top about 5.6 (e.g., at least about 5.1, at least about 5.2, at least about 5.3, at least about 5.4, at least about 5.5 or at least about 5.6) and/or at most about 5.6. In some embodiments, the pH-adjusted egg white can have a pH of 5.2 to 5.5. In some embodiments, the pH-adjusted egg white can have a pH of about 5.4. Without wishing to be bound by theory, it is believed that such a pH (e.g., about 5.4) can precipitate cellular impurities (e.g., proteins) and allow them to be filtered out before the viral inactivation step. In some embodiments, the reduction in cellular impurities during this process allows for a higher volume of material for downstream processing. In some embodiments, the reduction in cellular impurities during this process allows for a higher efficiency during downstream processing, e.g., faster purification, less expensive purification, higher purity purification, etc. In some embodiments, the pH of the first eluate is maintained until the first elate is filtered. In some embodiments, the pH off the first eluate is maintained until eluate undergoes a viral inactivation process.

In some embodiments, the pH of the second eluate is a value such that viral inactivation occurs. For example, the pH of the second eluate can have a pH of less than 4.5, less than 4.3, or less than 4.0. In some embodiments, the second eluate can have a pH of about 2 to about 4, about 2.2 to about 3.9, about 2.5 to about 3.9, about 2.7 to about 3.9, about 3 to about 3.9, about 3.3 to about 3.9, or about 3.5 to about 3.9. In some embodiments, the second eluate be adjusted to a pH of about 3.0 to about 4.0. Without wishing to be bound by theory, it is believed that such a pH (e.g., about 3 to about 4) can inactivate various viruses and virus-like particles by denaturing their viral coat proteins.

In general, the amounts of the acidic agent and the salt used in the acidic buffer can vary depending on the desired pH of the acidic buffer and the purification process. In some embodiments, the acidic buffer can have a pH from about 2.5 to about 6.5, about 3 to about 6.5, about 3.5 to about 6.5 or about 4.0 to about 6.5 (e.g., from about 4 to about 5 or from about 4 to about 4.5). For example, the acidic buffer can have a pH of about 4 or a pH of about 4.5.

The pH, concentration and identity of the acid buffer can remain the same, or can vary for one or more of the purification processes. For example, the pH, concentration and identity of the acid buffer can vary between the clarification process, the protein precipitation process, the viral inactivation process, and the neutralization process. In some embodiments, the same acid buffer is used for each of the purification processes. In some embodiments, more than one acid buffers can be used during a single purification process.

The acidic agent in the acidic buffer can generally be any suitable acid (e.g., an organic acid or an inorganic acid). Exemplary acidic agents include acetic acid, hydrochloric acid, sulfuric acid, nitric acid, phosphoric acid, hydrofluoric acid, hydrobromic acid, perchloric acid, citric acid, boric acid, tartaric acid, lactic acid, formic acid, oxalic acid, uric acid, and barbituric acid. In some embodiments, a combination of two or more (e.g., three or four) acids can be used as the acidic agent in the acidic buffer.

In some embodiments, the acidic buffer can include one or more salts (e.g., alkaline salts). An example of such a salt can be sodium acetate. In some embodiments, the salt used in the acidic buffer can be a salt of the acidic agent used in the acidic buffer. In other embodiments, the salt used in the acidic buffer can be a salt of an acid different from the acidic agent used in the acidic buffer. In some embodiments, the acidic buffer can include from about 5M to about 6M (e.g., about 5.7 M) of a salt (e.g., sodium acetate). Without wishing to be bound by theory, it is believed that using a salt having such a concentration can result in an acidic buffer having a suitable amount of buffering content. If the buffering content is too high, the acidic buffer may become flammable and/or corrosive, rendering the buffer unsafe to maintain, handle, and/or store. If the buffering content is too low, a larger volume of the acidic buffer might be needed to adjust the pH of the egg white to the target value, thereby reducing the efficiency of the egg white preparation process, as well as the downstream protein isolation/purification processes.

The acidic buffer can be formed by any suitable methods known in the art. For example, the acidic buffer can be formed by adding an acidic agent to a solution containing a base to adjust the pH of the solution to a desired value. For example, glacial acetic acid solution can be added to an appropriate amount of NaOH to obtain an acidic buffer containing 5.7M sodium acetate.

In general, the amount of the acidic buffer relative to that of the purification product to which it is being added (e.g., the pooled egg whites of the clarification process, the first eluate, the second filtrate or the pH adjusted second filtrate, etc.) is small. For example, the acidic buffer can be from about 0.5 wt % to about 5 wt % (e.g., from about 0.5 wt % to about 2 wt %, from about 0.7 wt % to 1.5 wt %, from about 0.9 wt % to about 1.4 wt %, from about 1 wt % to about 1.4%, or from about 1.1 wt % to about 1.3 wt %) per kilogram of the purification product. Conventionally, efforts to purify a heterologous protein from pooled egg whites using bulk chromatographic processing required adding an acidic buffer having a volume 2- to 5-fold (i.e., 200% to 500%) of the volume of the egg white as it was not expected that adding a small amount of an acidic buffer would be effective in adjusting the pH of the egg white to the target value. Such a process is not economically practical or feasible at a large manufacturing scale due to the size constraints of chromatographic columns and other manufacturing equipment used in the egg white preparation process. Unexpectedly, the present inventors discovered that bulk chromatographic processing can be achieved by adding a small amount of an acidic buffer (e.g., at most about 5 wt % per kilogram of purification product) relative to the amount of purification product, thereby significantly reducing the amount of the columns used in the chromatographic isolation processes, the sizes of other equipment used in these processes, and the cost and time of isolating heterologous proteins from egg whites.

Without wishing to be bound by theory, it is believed that additional advantages of adding a relatively smaller amount of an acidic buffer relative to the purification product include (1) negligible dilution of purification product, (2) essentially no change in conductivity, which allows for the precipitation of ovomucin-lysozyme complexes, which in turn reduces the viscosity of the egg white at lower pH range (e.g., pH 5-6.5) and facilitates separation of unwanted materials from the egg white during the filtration and chromatographic processes, and (3) minimizing formation of low pH pockets within the purification product that can potentially damage heterologous proteins or result in uneven pH of the purification product.

In general, the acidic buffer can have a conductivity ranging from about 8 mS/cm to about 40 mS/cm. For example, the acidic buffer can have a conductivity of at least about 8 mS/cm (e.g., at least about 9 mS/cm, at least about 10 mS/cm, at least about 11 mS/cm, at least about 12 mS/cm, at least about 13 mS/cm, at least about 14 mS/cm, at least about 15 mS/cm, at least about 16 mS/cm, at least about 17 mS/cm, at least about 18 mS/cm, at least about 19 mS/cm, at least about 20 mS/cm, at least about 21 mS/cm, at least about 22 mS/cm, at least about 23 mS/cm, at least about 24 mS/cm, at least about 25 mS/cm) and/or at most about 40 mS/cm (e.g., at most about 39 mS/cm, at most about 38 mS/cm, at most about 37 mS/cm, at most about 36 mS/cm, at most about 35 mS/cm, at most about 34 mS/cm, at most about 33 mS/cm, at most about 32 mS/cm, at most about 31 mS/cm, at most about 30 mS/cm, at most about 29 mS/cm, at most about 28 mS/cm, at most about 27 mS/cm, at most about 26 mS/cm, or at most about 25 mS/cm). For example, the acidic buffer can have a conductivity of any value between about 8 mS/cm and about 40 mS/cm. Without wishing to be bound by theory, it is believed that using an acidic buffer having a conductivity from about 8 mS/cm to about 40 mS/cm would minimize the changes to the conductivity of the purification product (e.g., egg white) so that the process can be implemented and streamlined with the downstream protein isolation step without changing the isolation conditions of the column chromatography used in the isolation step and without causing further precipitation or aggregation.

In some embodiments, the acidic buffer can be added to the purification product in a single bolus injection. In some embodiment, the single bolus injection is performed at a suitable injection rate (e.g., at least about 1 L/minute) to ensure that the addition of the acidic buffer is added within a suitable amount of time (e.g., at most about 5 minutes). In some embodiments, the acidic buffer is added at a rate of at least about 1% (vol/vol) per minute, 2% (vol/vol) per minute, 3% (vol/vol) per minute, 4% (vol/vol) per minute, 5% (vol/vol) per minute, 10% (vol/vol) per minute, 20% (vol/vol) per minute, or 30% (vol/vol) per minute. Without wishing to the bound by theory, it is believed that the advantages of using a single bolus injection may include (1) forming relatively large flocculent during clarification that settles easily under gravity, thereby reducing the need for large filters and (2) avoiding the need for continuous titration of a purification product, which can cause false pH readings that trigger repeated addition of an acid or a base, which in turn can potentially damage the heterologous proteins in the purification product.

In some embodiments, the acidic buffer can be titrated into the purification product over a period of time. In some embodiments, the acidic buffer is added while mixing the purification product to reduce unintended high concentration of acidic buffer in the purification product.

In some embodiments, after the acidic buffer is added to the purification product, the purification product is mixed at a suitable temperature, e.g., 2 to 8° C., 8 to 15° C., 15 to 20° C. or 20 to 30° C. In some embodiments, after the acidic buffer is added to the purification product, the purification product is mixed at 2 to 8° C. In some embodiments, the addition of the acidic buffer and the mixing of the egg white are performed concurrently.

In general, the purification product, e.g., the pH-adjusted egg white, has a relative low conductivity (e.g., similar to the conductivity of an egg white not treated with an acidic buffer). For example, the purification product, e.g., pH-adjusted pH-adjusted egg white, can have a conductivity of at least about 8 mS/cm (e.g., at least about 8.2 mS/cm, at least about 8.4 mS/cm, at least about 8.6 mS/cm, at least about 8.8 mS/cm, at least about 9 mS/cm, at least about 9.2 mS/cm, at least about 9.4 mS/cm, at least about 9.6 mS/cm, at least about 9.8 mS/cm, at least about 10 mS/cm, at least about 11 mS/cm, at least about 12 mS/cm, at least about 13 mS/cm, or at least about 14 mS/cm) and/or at most about 20 mS/cm (e.g., at most about 19 mS/cm, at most about 18 mS/cm, at most about 17 mS/cm, at most about 16 mS/cm, at most about 15 mS/cm, at most about 14 mS/cm, at most about 13 mS/cm, at most about 12 mS/cm, at most about 11.8 mS/cm, at most about 11.6 mS/cm, at most about 11.4 mS/cm, at most about 11.2 mS/cm, at most about 11 mS/cm, at most about 10.8 mS/cm, at most about 10.6 mS/cm, at most about 10.4 mS/cm, at most about 10.2 mS/cm, or at most about 10 mS/cm). For example, the purification product, e.g., pH-adjusted pH-adjusted egg white, can have a conductivity of any value between about 8 mS/cm and about 20 mS/cm. Without wishing to be bound by theory, it is believed that keeping the purification product, e.g., pH-adjusted pH-adjusted egg white, at conductivity from about 8 mS/cm to about 20 mS/cm would allow the purification product to comply with the conditions used in the downstream protein isolation step so that the purification product can be consistently used in the isolation step without changing the isolation conditions of the column chromatography used in this step.

In some embodiments, the pH-adjusted egg whites have reduced viscosity to aid in reducing filter caking. In some embodiments, the pH-adjusted egg whites have a viscosity of less than 0.01 Pa/s, less than 0.005 Pa/s, less than 0.002 Pa/s, or less than 0.001 Pa/s as determined using a rate-controlled rheometer (e.g., Rheolyst, type AR-1000-N, TA Instruments, New Castle, Del.).

Purification Processes

The disclosure of the present invention relates to number of purification processes which, when performed together, result in the efficient purification of a heterologous protein. These process include, but are not necessarily limited to, (1) a clarification process, (2) a hydrophobic interaction chromatography process, (3) a viral inactivation process, and (4) an anion exchange process. The purification process can further include, a nanofiltration process, an anion exchange process, a second hydrophobic exchange process, and/or an ultrafiltration/diafiltration process. The processes as described herein can be used in various orders of operation, e.g., the viral inactivation process can be performed either before or after the anion exchange process, however, the clarification process generally occurs before any of the remaining processes. In some embodiments, the disclosure provides for a specific order of operation including (1) a clarification process, (2) a hydrophobic interaction chromatography (HIC) process, (3) a viral inactivation process, and (4) an anion exchange process. One of skill in the art, reading the present disclosure, will also appreciate that other processes can be included between each of the listed purification processes. For example, as disclosed herein, additional filtration processes can occur between the clarification process and the HIC process, and between the HIC process and the viral inactivation process.

In some embodiments, the egg white used as a starting material of the methods described herein can include a recombinant protein (e.g., a heterologous protein, e.g., a recombinant therapeutic protein) exogenous to the egg white. Exemplary heterologous proteins include cytokines such as GC-SF, GM-CSF, erythropoietin, and interferons such as interferon-α or interferon-β; human lysosomal enzymes; immunoglobulins (e.g., antibodies); and structural proteins. Other exemplary heterologous proteins that can be isolated from bulk chromatographic processing have been described, e.g., in U.S. Application Publication Nos. 2009/0299037 and 2015/0307547.

In some embodiments, the heterologous protein is sebelipase alfa. Sebelipase alfa can be purified from the egg whites of eggs from transgenic G. gallus hens carrying the rhLAL gene. Sebelipase alfa is a monomeric glycoprotein containing 6 N-linked glycosylation sites and has a molecular mass of approximately 55,000 daltons. The amino acid sequence for sebelipase alfa is the same as the amino acid sequence for human LAL. Sebelipase alfa is marketed under the tradename KANUMA (Alexion, New Haven Conn.), as described, e.g., in U.S. Pat. No. 8,663,631 and WO2011/133960.

In general, the methods of purifying a heterologous protein from an egg white described herein include (1) adding an suitable amount of an acidic buffer (e.g., from about 0.5 wt % to about 5 wt % per kilogram of the egg white) containing an acidic agent to a pool of egg white (e.g., having a volume of at least about 10 liters); and mixing to form a pH-adjusted egg white having a pH ranging from about 5.8 to 6.5), (2) filtering the pH-adjusted egg white and collecting the first filtrate, (3) subjecting the first filtrate to hydrophobic interaction chromatography matrix, and collecting a first eluate comprising the heterologous protein; (d) adjusting the pH of the first eluate of (c) to a pH of 5.0 to 5.6 to form a pH-adjusted eluate; (e) filtering the pH-adjusted eluate to obtain a second filtrate; (f) adjusting the pH of the second filtrate to a pH of 3.0 to 4.0 to form a pH-adjusted second filtrate; (g) neutralizing the pH-adjusted second filtrate of (f) to a pH of 5.0 to 8.0 to form a neutralized solution; (h) subjecting the neutralized solution to a cation exchange chromatography matrix and collecting a second eluate comprising the heterologous protein.

It is noted that throughout the specification, the terms "first," "second," "third," etc., are used when referring to specific aspects of the purification process, e.g., "first filtrate," "second fitrate," etc. For clarity, the designations "first," "second," "third," etc., are to assist with nomenclature to distinguish the existence of different process, and are not limiting with regards to order or number. For example, the disclosure envisions that the skilled artisan could perform a third filtration process between the "first filtrate" and "second filtrate," thus forming a third filtrate which is formed before the second filtrate.

The egg white pool used in the present invention can include various volumes, but can be particularly advantageous for larger volumes. In general, the egg white pool used in the methods described herein is at an industrial scale and has a relatively large volume. For example, the egg white pool can have a volume of at least about 1 liter, at least about 10 liters (e.g., at least about 50 liters, at least about 100 liters, at least about 200 liters, at least about 300 liters, at least about 400 liters, at least about 500 liters, at least about 600 liters, at least about 700 liters, at least about 800 liters, at least about 900 liters, at least about 1,000 liters, at least about 1,500 liters, at least about 2,000 liters, at least about 3,000 liters, at least about 4,000 liters, at least about 5,000 liters, at least about 10,000 liters, or at least about 20,000 liters). Methods of preparing egg white as a starting material to be used in the methods described herein have been described, e.g., in U.S. Application Publication No. 2009/0299037 and 2015/0307547.

The term "clarification" refers to an initial purification step wherein the pooled egg whites are acidified and become less viscous, and some insoluble proteins are removed from the pooled egg whites. A generic, non-limiting, schematic of a clarification process can be found in FIG. 3. In some embodiments, the acidified pooled egg whites settle for a suitable period of time (e.g., at least about 6 hours) such that the egg white separates into top, middle and bottom layers. Typically, the top layer includes certain unwanted materials (e.g., denatured protein and foamy lipids including phospholipids, triglyceride, and cholesterol) having a low density, the bottom layer includes the precipitates formed from the egg white proteins (e.g., ovomucin-lysozyme complexes), and the middle layer includes a relatively clear egg white solution. Generally, clarification is conducted at 2 to 8° C.

In some embodiments, during clarification, if the pH of the pH-adjusted egg white becomes falling outside the desired value (e.g., 5.7±0.1, 6.0±0.1, or 6.3±0.1), it can be adjusted to reach the desired value by using an acid (e.g., the acidic buffer described above) or a base (e.g., a 5.7 M sodium acetate or 1 N sodium hydroxide solution). In such embodiments, the pH adjustment can be followed by additional mixing (e.g., for at least about 1 hour) and settling (e.g., for at least about 3 hours) at room temperature. In general, the total mixing and settling time during clarification does not exceed 24 hours to minimize the time that the heterologous proteins in the egg white are exposed to the processing environment, thereby maintaining the biological activities of these proteins.

In some embodiments, clarification can include a step of isolating the middle layer from the pH-adjusted egg white after the settling step. In general, the middle layer can be isolated by using methods known in the art. For example, the middle layer can be siphoned out of the vessel containing the pH-adjusted egg white by inserting a tube (e.g., a metal or polycarbonate tube) into the middle layer (preferably in the center of the middle layer) so that the content of the middle layer can be pumped into a receiving vessel without disturbing the top and bottom layers.

In general, during clarification, the pH-adjusted egg whites can be filtered to remove any particles suspended in the middle layer to obtain a homogeneous, low viscosity, clear egg white solution. In some embodiments, the pH-adjusted egg whites can be filtered through one or more filters having an average pore size at most about 100 µm (e.g., at most about 90 µm, at most about 80 µm, at most about 70 µm, at most about 60 µm, at most about 50 µm, at most about 40 µm, at most about 30 µm, at most about 20 µm, at most about 10 µm, at most about 9 µm, at most about 8 µm, at most about 7 µm, at most about 6 µm, at most about 5 µm, at most about 4 µm, at most about 3 µm, at most about 2 µm, or at most about 1 µm) and/or at least about 0.1 µm (e.g., at least about 0.2 µm, at least about 0.3 µm, at least about 0.4 µm, at least about 0.5 µm, at least about 0.6 µm, at least about 0.7 µm, at least about 0.8 µm, at least about 0.9 µm, at least about 1 µm, at least about 2 µm, or at least about 3 µm). For example, the filter can have an average pore size ranging from about 0.1 µm to about 100 µm (e.g., from about 0.1 µm to about 40 µm, from about 40 µm to about 100 µm, from about 3 µm to about 6 µm, or from about 0.1 µm to about 0.3 µm).

In some embodiments, filtering of the pH-adjusted egg whites can occur through a plurality of filters serially connected to each other, in which the average pore size of the filters decreases sequentially. For example, the pH-adjusted egg whites can be filtered through a filtration system containing three serially connected filters, in which the first filter can have an average pore size of about 40 µm, the second filter can have an average pore size from about 3 µm to about 6 µm, and the third filter can have an average pore size from about 0.1 µm to about 0.3 µm. An example of such a filtration system is a system containing sequential depth filters commercially available from Pall Corporation (e.g., containing T2600, K200P and Bio10 depth filters). Optionally, the filtration system can further include a fourth filter (e.g., having an average pore size about 0.2 µm) downstream of the third filter. An example of the fourth filter is a Sartobran P filter available from Sartorius Corporation.

In some embodiments, the filters used in clarification can have a large filtration medium area. For example, the filters can have a filtration medium area of at least about 1 $m^2$ (e.g., at least about 2 $m^2$, at least about 4 $m^2$, at least about 6 $m^2$, or at least about 8 $m^2$).

In some embodiments, after the acidic buffer and the egg white are mixed to form a pH-adjusted egg white, the pH-adjusted egg white can be filtered without the need to allow the precipitates in the pH-adjusted egg white to settle. In such embodiments, the pH-adjusted egg white (including the precipitates formed during the addition/mixing steps and the remaining egg white solution) can be filtered without any prior separation of the precipitates from the pH-adjusted egg white. For example, after the acidic buffer and the egg white are mixed, the pH-adjusted egg white can be filtered without settling by using one or more filters described herein (e.g., a filtration system containing three serially connected filters having decreasing pore sizes). Without wishing to be bound by theory, it is believed that, by eliminating a settling step, such a method can significantly reduce the time and costs for preparing egg white for bulk chromatographic processing and for isolating heterologous proteins from the egg white.

In some embodiments, after the acidic buffer and the egg white are mixed to form a pH-adjusted egg white, the pH-adjusted egg white can be centrifuged to separate precipitates (e.g., ovomucin-lysozyme complexes) from the supernatant. The supernatant thus obtained can then be filtered by using one or more filters described herein.

In general, the filtered egg white solution can be used to isolate heterologous proteins by using column chromatography, such as ion exchange chromatography or chromatography based on hydrophobic interaction. Examples of such chromatographic methods have been described, e.g., in U.S. Application Publication No. 2009/0299037.

In some embodiments, the filter is pre-treated with a buffer prior to filtration. The pre-treatment buffer can be used to wet the filter prior to passing the egg white (e.g., pH-adjusted egg white). The pre-treatment buffer can include one or more salts (e.g., alkaline salts). Exemplary salts include sodium phosphate and sodium chloride. In some embodiments, the pre-treatment buffer can include a combination of sodium phosphate and sodium chloride. In general, the pre-treatment buffer can include an acid. Exemplary acids include acetic acid, hydrochloric acid, sulfuric acid, nitric acid, phosphoric acid, hydrofluoric acid, hydrobromic acid, perchloric acid, citric acid, boric acid, tartaric acid, lactic acid, formic acid, oxalic acid, uric acid, and barbituric acid. In some embodiments, a combination of two or more (e.g., three or four) acids can be used in the pre-treatment buffer.

In some embodiments, the pre-treatment buffer can have a pH substantially the same as the pH of the egg white. For example, the pre-treatment buffer can have a pH at least about 5.8 to 6.5. In some embodiments, the pre-treatment buffer can have a pH of about 6. Without wishing to be bound by theory, it is believed that using a pre-treatment buffer having a pH substantially the same as the pH of the egg white to treat a filter can adjust the pH of the filter surface to be similar to the pH of the egg white, thereby minimizing precipitation of the egg white during filtration, which can cause blockage in the filter or obstruct the flow of the samples that causes shear stress on the filter, thereby seriously shortening the usage life of the filter.

In some embodiments, the pH-adjusted egg white can be passed through a filter during clarification under a relatively small differential pressure (e.g., less than about 30 psi, less than about 25 psi, less than about 20 psi, less than about 15 psi, less than about 12 psi, less than about 10 psi, or less than about 5 psi). Without wishing to be bound by theory, it is believed that passing the egg white through a filter under a relatively small differential pressure can minimize damages and/or blockage to the filter, thereby reducing product costs as the filter can be very expensive.

As used herein, the term "first filtrate" refers to the clarified egg white product of the filtration of the pH-adjusted egg whites, independent of whether the pH-adjusted egg whites isolated using centrifugation or other means. In some embodiments, the method of the disclosure comprises centrifuging the pH-adjusted egg white to collect a fraction comprising sebelipase alfa, and then subjecting the fraction comprising sebelipase alfa to the filtering in (b). The first filtrate can be collected and used in further purification processes, e.g., the first filtrate can be subjected to a hydrophobic interaction chromatography matrix. In some embodiments, the first filtrate is adjusted to 20 to 30° C. (e.g., room temperature), or alternatively, is adjusted to 2 to 8° C.

Certain embodiments of the invention provide for a method comprising one or more hydrophobic interaction chromatography ("HIC") matrices. See, e.g., FIG. 4. A suitable HIC column is one whose stationary phase comprises hydrophobic groups. In some embodiments, the hydrophobic interaction chromatography matrix is a phenyl, octyl, or butyl hydrophobic interaction matrix. A non-limiting example of such a HIC matrix is a Phenyl HP Sepharose™ column. Inclusion of one or more HIC processes can facilitate the reduction or elimination of one or more cellular protein impurities. In certain embodiments the HIC process employs a high salt buffer to promote interaction of heterologous proteins (or aggregations thereof) with the hydrophobic column. The HIC process can be equilibrated with an equilibration buffer prior to loading of the purification product. In some embodiments, the HIC process follows the clarification process. In some embodiments, the HIC process following the clarification process is a phenyl hydrophobic interaction chromatography matrix. One of skill in the art will appreciate that the HIC process can use one or more washes with the appropriate wash buffers during the HIC process. The product of the HIC process (the eluted product) is referred to herein as the "first eluate."

In some embodiments, the method of purifying the heterologous protein comprises precipitation of impurities by adjusting the purification product to pH 5.0 to 5.6. See, e.g., FIG. 5. In some embodiments, precipitation of protein impurities by lowering the pH can follow the HIC process, i.e., it can be performed on the first eluate. Precipitation of protein impurities by lowering the pH can occur for greater than 20 minutes, greater than 1 hour, greater than 2 hours, greater than 4 hours, greater than 8 hours, greater than 12 hours, greater than 18 hours, greater than 24 hours, or greater than 48 hours, but should not exceed 72 hours. In some embodiments, the precipitation of protein impurities by lowering the pH can occur at a temperature of 15 to 30° C., or 18 to 25° C. The product of the precipitation of protein impurities by lowering the pH is termed "pH-adjusted eluate."

In some embodiments, the pH-adjusted eluate is filtered to remove additional impurities. In some embodiments, the filter is a depth filter. The term "depth filter" is a term of art and means a filter that includes a porous filtration medium that captures contaminants and/or impurities (such as any of the contaminants and/or impurities described herein) within its 3-dimensional structure and not merely on the surface. Depth filters are characterized in that they retain the contaminants or impurities within the filter and can retain a relatively large quantity before becoming clogged. Depth filter construction may comprise multiple layers, multiple membranes, a single layer, or a resin material. Non-limiting examples of depth filters include CUNO® Zeta PLUS® Delipid filters (3M, St. Paul, Minn.), CUNO® Emphaze AEX filters (3M, St. Paul, Minn.), CUNO® 90ZA08A filters (3M, St. Paul, Minn.), CUNO® DELI08A Delipid filters (3M, St. Paul, Minn.), Millipore XOHC filters (EMD Millipore, Billerica, Mass.), MILLISTAK® pads (EMD Millipore, Billerica, Mass.). The filter used on the pH-adjusted eluate can be of various pore sizes, depending on the heterologous protein to be purified. In some embodiments, the filter is a 0.1 µm, 0.2 µm, 0.4 µm, 0.5 µm, 1 µm, or 2 µm filter. The product of the filtering of the pH-adjusted eluate is termed "second filtrate."

The process of the present invention comprises a virus inactivating process whereby the pH of a purification product is adjusted to a pH of 3.0 to 4.0. See, e.g., FIG. 5. In some embodiments, the virus inactivating process comprises adjusting the pH of the purification product to a pH of 3.2 to 3.6. The pH-adjusted purification product (i.e., the "pH-adjusted second filtrate") can be maintained at the low pH (pH 3.0 to 4.0) for greater than 10 minutes, greater than 20 minutes, greater than 30 minutes, greater than 40 minutes, greater than 60 minutes, or greater than 60 minutes. In some embodiments, the pH-adjusted second filtrate can be maintained at the low pH (pH 3.0 to 4.0) for 10 minutes to 120 minutes, 10 minutes to 90 minutes, 20 minutes to 90 minutes, 30 minutes to 90 minutes, 40 minutes to 90 minutes, 50 minutes to 90 minutes, or 60 minutes to 90 minutes. In some embodiments, the pH-adjusted second filtrate can be maintained at the low pH (pH 3.0 to 4.0) for 10 minutes to 60 minutes, 10 minutes to 50 minutes, 10 minutes to 40 minutes or 10 minutes to 30 minutes. In some embodiments, the pH-adjusted second filtrate can be maintained at the low pH (pH 3.0 to 4.0) at a temperature of 10° C. to 30° C., or 18° C. to 25° C. for the duration of the viral inactivation process.

Following the viral inactivation process, the pH of the purification product can be adjusted to prepare the purification product for the next purification process. In some embodiments, the pH can be adjusted to a pH of 5.0 to 8.0 to form a neutralized solution. The pH can be adjusted using any basic buffer known in the art, including, but not limited to an amine, ammonia, a carbonate, a bicarbonate, a borate and a phosphate. In some embodiments, the neutralized solution is subjected to further processing steps. In some embodiments, the neutralized solution is subjected to a cation exchange chromatography matrix. See, e.g., FIG. 6. The cation exchange chromatography process utilized in this invention may use any cation exchange chromatography process known in the art, for example, a matrix comprising a methyl sulfonate group, diethylaminoethyl group or an ammonium group. In an embodiment, the cation exchange chromatography step may be accomplished by using a column packed with Poros XS resin (Life Technologies) or Toyopearl GigaCap S matrix (Tosoh Bioscience LLC, Yamaguchi 746-8501, Japan). In a particular embodiment, the cation exchange chromatography step may be operated in bind-elute mode. In some embodiments, the heterologous protein of interest is eluted from the cation exchange chromatography matrix using an increasing salt gradient. The product of the cation exchange chromatography matrix comprising the heterologous protein is termed the "second eluate."

In some embodiments, the purification product is subjected to nanofiltration. See, e.g., FIG. 7. Any suitable nanofiltration device can be used. In certain embodiments, the nanofiltration device will have a mean pore size of between about 15 nm and about 200 nm. Examples of nanofilters suitable for this use include, without limitation, DVD, DV 50, DV 20 (Pall), Viresolve NFP, Viresolve NFR (Millipore), Planova 15N, 20N, 35N, and 75N (Planova). In a specific embodiment, the nanofilter may have a mean pore size of between about 15 nm and about 72 nm, or between about 19 nm and about 35 nm, or of about 15 nm, 19 nm, 35 nm, or 72 nm. In a preferred embodiment, the nanofilter will have a mean pore size of about 35 nm, such as an Asahi PLANOVA 35N filter or equivalent thereof. The surface area of the nanofilter can vary depending on the concentration and volume of the purification product. In some embodiments, the nanofilter has a surface area of greater than 0.1 $m^2$, 0.2 $m^2$, 0.5 $m^2$, 1 $m^2$, 1.5 $m^2$, 2 $m^2$, 2.5 $m^2$ or 3 $m^2$. In some embodiments, the nanofilter has a surface area of 2.1 $m^2$. The product of the nanofiltration is termed the "third filtrate."

In some embodiments, the method of purifying the heterologous protein comprises subjecting the purification product to an anion exchange chromatography matrix. See, e.g., FIG. 8. The principles of anion exchange chromatography are well known in the art, but, briefly, relies on the charge-charge interactions between the particles to be isolated and the charge on the resin used. The column usually contains immobilized positively charged moieties. Generally, these are quaternary amino groups (Q resins) or diethylaminoethane groups (DEAE resin). Examples of commercially available anion exchange resins useful in the practice of the present disclosure include, but are not limited to, the Mustang® Q (Pall Life Sciences) and the Fractogel TMAE (Merck) resins. Traditional anion exchange resins include those used in the bead format, for example Q Sepharose™ available from GE Healthcare Bio-Sciences AB. Thus, in one embodiment, the anion exchange chromatography comprises a bead-based chromatography resin. However, throughput limitations of bead-based systems require large volume columns to effectively capture impurities. In bead-based chromatography, most of the available surface area for adsorption is internal to the bead. Consequently, the separation process is inherently slow since the rate of mass transport is typically controlled by pore diffusion.

In another embodiment, the anion exchange chromatography comprises a membrane-based chromatography resin, such as the Mustang® Q resin. Membrane-based chromatographic systems have the ligands attached directly to the convective membrane pores, thereby reducing the effects of internal pore diffusion on mass transport.

In some embodiments, the methods of purifying the heterologous protein comprises a second HIC purification process. The second HIC purification process can be the same, or a different matrix than was used in the first HIC matrix. In some embodiments, the second hydrophobic interaction chromatography matrix is a phenyl, octyl, or butyl hydrophobic interaction matrix. In some embodiments, the second HIC matrix is a butyl-HIC. See, e.g., FIG. 9. In certain embodiments the second HIC process employs a high salt buffer to promote interaction of heterologous proteins (or aggregations thereof) with the hydrophobic column. The second HIC process can be equilibrated with an equilibration buffer prior to loading of the purification product. One of skill in the art will appreciate that the second HIC process can use one or more washes with the appropriate wash buffers during the second HIC process. The product of the HIC process (the eluted product) is referred to herein as the "fourth eluate."

The present invention provides for processes comprising various filters. The skilled artisan can appreciate that dead end, depth, and Tangential Flow Filtration (TFF) (also referred to as Cross Flow Filtration CFF) is envisioned by this disclosure for each of the filters discussed. In some embodiments, TFF is used in the purification process, especially when dealing with larger volumes and higher concentrations of purification product. TFF is well known to those of skill in the art and equipment and protocols for its implementation in a wide range of situations are commercially available from a variety of manufacturers including but not limited to the Pall Corporation, Port Washington, N.Y. and Spectrum Labs, Rancho Dominguez, Calif. Generally, TFF involves the recirculation of the retentate across the surface of the membrane. This gentle cross flow feed minimizes membrane fouling, maintains a high filtration rate and provides high product recovery. In one embodiment, the TFF step may be implemented with a flat sheet system. Flat sheet systems can be used in large scale production where such systems are provided with a means (e.g., an open flow channel) to prevent excessive shear forces on the enveloped viral particles. Alternatively, the TFF step may be implemented with a hollow fiber system.

In some embodiments, ultrafiltration/diafiltration may be performed to further concentrate the purification product. See, e.g., FIG. 10. In some embodiments, the ultrafiltration/diafiltration may performed after the anion exchange chromatography process, i.e., the ultrafiltration/diafiltration may performed on the nanofiltrate, or the fourth eluate. In one embodiment, the fourth eluate may be concentrated by ultrafiltration to a protein concentration of between about 2% and about 10% (w/v). In certain embodiments, the ultrafiltration is carried out in a cassette with an open channel screen and the ultrafiltration membrane has a nominal molecular weight cut off (NMWCO) of less than about 100 kDa or less than about 90, 80, 70, 60, 50, 40, 30, or fewer kDa. In some embodiments, the ultrafiltration membrane has a NMWCO of no more than 50 kDa.

Upon completion of the ultrafiltration step, the concentrate may further be concentrated via diafiltration. In certain embodiments, the diafiltration solution may comprise a stabilizing and/or buffering agent. In a preferred embodiment, the stabilizing and buffering agent is glycine at an appropriate concentration.

Typically, the minimum exchange volume is at least about 3 times the original concentrate volume or at least about 4, 5, 6, 7, 8, 9, or more times the original concentrate volume. Typically, at the end of the concentration process, the pH of the solution will be between about 6.0 to 7.5.

In some embodiments, the methods describe herein result in a product containing the heterologous protein which is pharmaceutically acceptable. As used herein, the term "pharmaceutically acceptable" refers to those compositions and/or dosage forms comprising the heterologous protein which are, within the scope of sound medical judgment, suitable for use in contact with the tissues of human beings and animals without excessive toxicity, irritation, allergic response, or other problem or complication, commensurate with a reasonable benefit/risk ratio. In some embodiments, the purified heterologous protein is suitable for intravenous administration.

In some embodiments, the purified heterologous protein described herein can be used for the treatment of a disease or condition. In some embodiments, the purified heterologous protein made by the methods described herein have higher protein purity, higher activity, more stability, or lower manufacturing costs relative to the heterologous protein made by a method previously known in the art. For example, if the method of the present invention is used to purify sebelipase alfa, the purified sebelipase alfa may have a higher protein purity, higher activity, more stability, or lower manufacturing costs relative to the sebelipase alfa made by a method previously known in the art. In some embodiments, the disclosure is directed to a product (e.g., sebelipase alfa) made by the methods described herein. In some embodiments, the purified heterologous protein (e.g., sebelipase alfa) is used for the treatment of a disease or condition (e.g., the treatment of patients with a diagnosis of Lysosomal Acid Lipase (LAL) deficiency). The terms "treat", "treating" or "treatment" include administering a therapeutically effective amount of a compound sufficient to reduce or eliminate at least one symptom of the state, disease or disorder The contents of all publications cited herein (e.g., patents, patent application publications, and articles) are hereby incorporated by reference in their entirety.

EXAMPLES

Example 1: Purification of Sebelipase Alfa

Description of Manufacturing Process and Process Controls

A process for the production of sebelipase alfa, recombinant human lysosomal acid lipase (rhLAL), using transgenic *Gallus gallus* was developed that expressed sebelipase alfa in egg whites (EW). Sebelipase alfa was purified from EW using conventional chromatographic methods in a specific order and at specified pH level. The purification process also incorporated additional specific steps for viral reduction. FIG. 1 outlines the steps in the sebelipase alfa production process.

EW was harvested, pooled and frozen for storage. Upon thaw for initiation of purification, pooled EW was pH adjusted and clarified by dead end filtration. The sebelipase alfa in clarified EW was then captured by hydrophobic interaction chromatography (Phenyl-HIC, PHIC), followed by precipitation at pH 5.4, a low pH viral inactivation step, DTT treatment, purification using cation exchange chromatography, nanofiltration, anion exchange membrane chromatography (quaternary amine), and hydrophobic interaction chromatography (Butyl-HIC, BHIC) as described below. The Butyl-HIC eluate was pH adjusted to yield the unformulated drug substance. The unformulated drug substance is concentrated, diafiltered and formulated with the addition of human serum albumin (HSA) to yield the final drug substance.

Single use disposable systems, or single use mixers (SUM), were used throughout processing. All filters were single use. Gamma-irradiated, single use disposable bags and connectors were used for buffers and product intermediates. All product contact materials were assessed with respect to USP Class VI requirements.

Throughout the downstream process, intermediates were held at room temperature (18-25° C.) if processing to the next unit operation continues within specified time intervals of less than 1 day. Applicants note that process intermediates may be held at 2-80° C. to minimize the potential for microbial growth at steps where chemical stability has been demonstrated. Where hold times exceed 24 hours, samples for bioburden were taken at the end of hold times to confirm microbial control.

Process intermediates were collected and stored in bags contained within process vessels, which were moved between or within processing suites as needed. Prepared buffers and solutions were held in storage bags, with buffer transfer totes for larger volumes. If product was chilled for holding, the process vessels were jacketed and connected to a cooling system to maintain temperature. Applicants note the product may be warmed to processing temperature using the same system.

The purification process had target set points for each step that were established based upon process development and process characterization data. These set points are included in the process narrative below. Control limits and operational ranges for each process step evaluated during validation reflected specific system hardware and equipment capabilities and thus may be tighter than development ranges. During routine processing, excursions outside operational ranges prompted the initiation of a deviation and an assessment of potential for product impact. Events determined to have potential impact on product quality were investigated and the material was dispositioned accordingly.

The following sections provide information on each unit operation in the sebelipase alfa manufacturing process as identified in FIG. 1.

Process Description Summary

Egg Collection and EW Harvest

Figure 2:
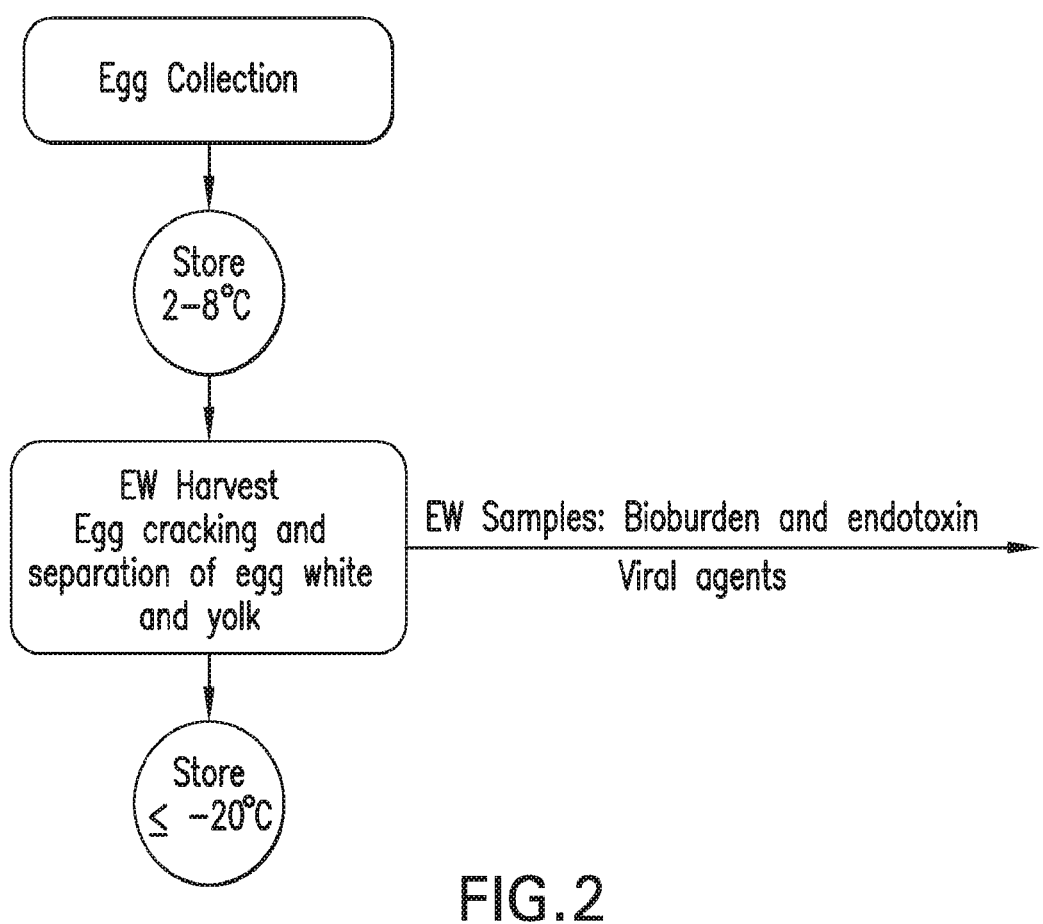
FIG. 2: Schematic representation of the egg collection and egg white harvest of transgenic eggs comprising sebelipase alfa of Example 1.

EW from transgenic *G. gallus* hens carrying the rhLAL gene was the starting material for the manufacturing process. The pooled EW were held at 2-8° C. The maximum hold time was ≤5 days. FIG. 2 provides a graphic representation of egg collection and EW harvesting.

Clarification

The purpose of the clarification step was to acidify the pooled EW and reduce the viscosity of the solution. The acidification also resulted in some protein precipitation.

The thawed egg white was pooled into an appropriately sized polypropylene tank (25 L) with sterile media liner (Thermo Scientific/Hyclone P/N 343050-0005). The pooled egg white was mixed to homogeneity using an overhead mixer (330 rpm) at 2-8° C. The pooled egg white was then conditioned to the target pH through addition of 5.7 M sodium acetate at pH 4.0. Table 6 lists the volume of the 5.7 M sodium acetate added for each clarification run to achieve the target pH. The pH was monitored for more than 2 hours to ensure target pH was achieved.

Figure 3:
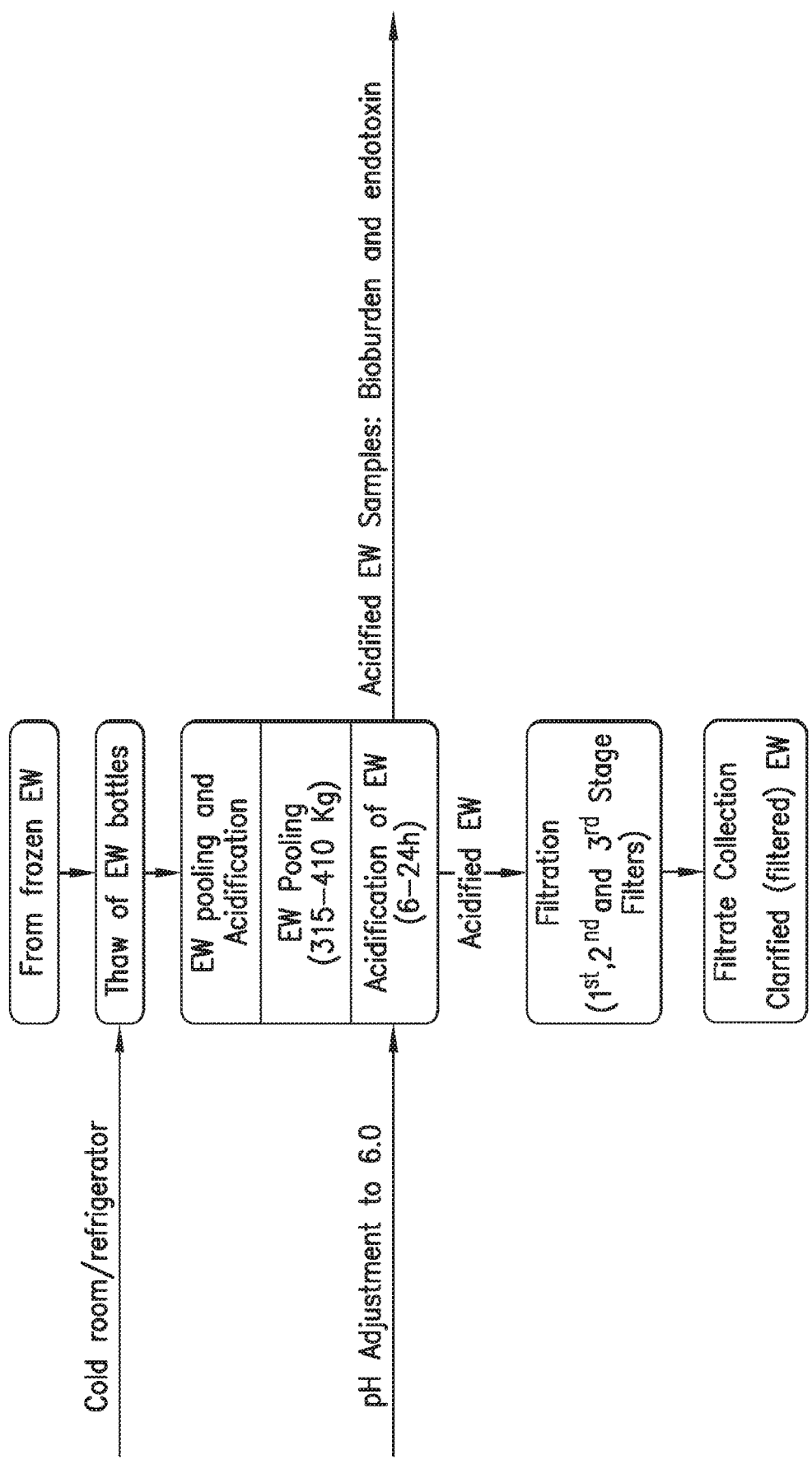
FIG. 3: Schematic representation of the clarification process of Example 1, used to reduce the viscosity of the egg white solution.

Filtration of the acidified EW solution resulted in a reduction in particulates and allowed for processing through the first chromatography step. The maximum hold time was ≤24 hours. FIG. 3 provides for a schematic representation of the clarification step.

Phenyl Hydrophobic Interaction Chromatography

The purpose of the phenyl-HIC step was to capture sebelipase alfa from the clarified EW and reduce the levels of EW protein impurities. Prior to filtration, filters were flushed individually with 80 L/m$^2$ with filtered RO/DI water. During the water flush, the holdup volume for each filtered was empirically determined. Upon completion of the water flush, the filters were plumbed into a continuous train and flushed with 16 L/m$^2$ of PHIC equilibration buffer (20 mM sodium phosphate, 140 mM sodium chloride, pH 6.0). Buffer flush ended when pH and conductivity of the effluent met flush buffer specifications (e.g., pH 6.0±0.1, conductivity 16.0±2.0). Pooled egg white was loaded onto the filter train using a ⅜" dip tube (I/P 73 tubing Cole) at 1.0 L/min with continuous mixing (overhead mixer, 300 rpm). 80% of the measured, cumulative hold up volume (~13.2 L) was collected and directed to waste. Filtrate was then collected in a separate appropriately sized container until the congealed low density precipitate entered dip tube. Filtration train was then flushed with 1.5 hold up volumes (~25 L) with a buffer equilibration buffer. The final filtrate was mixed well using a clean tank paddle to ensure homogeneity prior to sampling. Filtrate was stored at 2-8° C. overnight prior to PHIC separation.

Prior to PHIC separation, filtrate stored at 2-8° C. was warmed using a room temperature water bath. The filtrate was secondarily filtered through a Sartobran 150 cartridge (0.45 um/0.22 um, P/N 5231307H4-00) to generate the final PHIC load. Table 1 lists the buffers and in-process parameters used.

TABLE 1

PHIC Chromatography Unit Operation

| Step | Buffer | CV | Linear Velocity (cm/h) | Flow Rate (mL/min) |
|---|---|---|---|---|
| Equilibration | 20 mM Sodium Phosphate, 140 mM NaCl, pH 6.0 | 5 | 120 cm/h | 4.02 |
| Loading | | | 60 cm/h | 2.01 |
| Wash 1 | 5 mM Sodium Phosphate, pH 6.0 | 8 | 120 cm/h | 2.01 (1CV) 4.02 (7CV) |
| Wash 2 | 5 mM Tris, 1M NaCl, pH 7.2 | 8 | 120 cm/h | 4.02 |
| Wash 3 | 5 mM Tris, 0.25M NaCl, pH 7.2 | 4 | 120 cm/h | 4.02 |
| Pre-Elution | 5 mM Tris, 17% IPA, pH 7.2 | UV→ 40 mAU | 120 cm/h | 4.02 |
| Fraction 1 | 5 mM Tris, 17% IPA, pH 7.2 | UV → 800 mAU | 120 cm/h | 4.02 |
| Elution | 5 mM Tris, 17% IPA, pH 7.2 | 1.9 | 120 cm/h | 4.02 |
| Post Elution | 5 mM Tris, 17% IPA, pH 7.2 | 2.0 | 120 cm/h | 4.02 |
| Strip | RO/DI | 5 | 60 cm/h Upflow | 2.01 |
| Acid Cleaning | 0.85% Phosphoric Acid | 3 | 60 cm/h upflow | 2.01 |
| Water Rinse | RO/DI | 5 | 60 cm/h; Upflow | 2.01 |
| CIP | 0.5N NaOH | 3 | 60 cm/h; Upflow; (1 h hold) | 2.01 |
| Water Rinse | RO/DI | 5 | 60 cm/h; upflow | 2.01 |
| Storage | 20% Ethanol | 3 | 60 cm/h; upflow | 2.01 |

Figure 4:
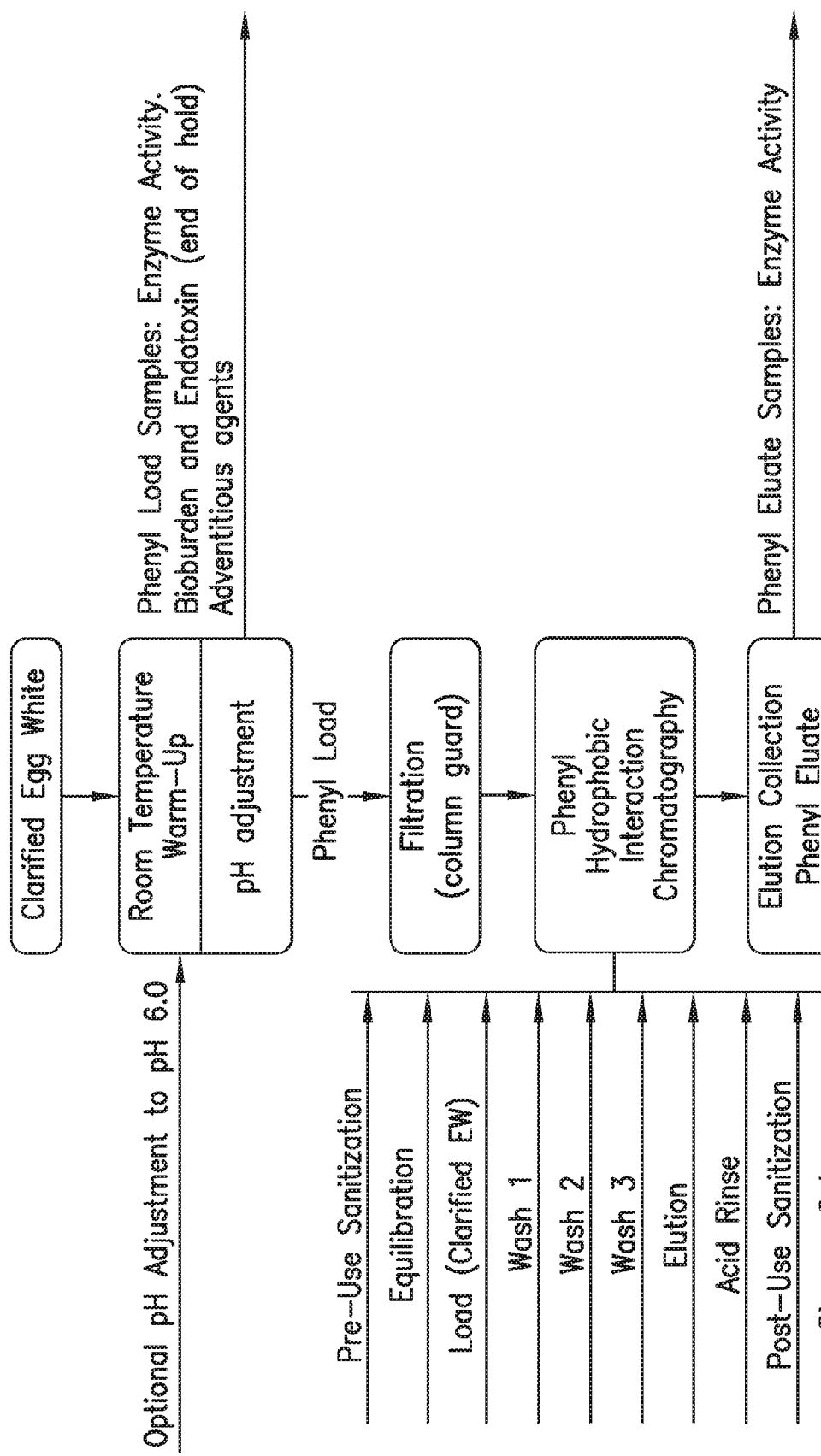
FIG. 4: Schematic representation of the phenyl hydrophobic interaction chromatography process of Example 1, used to reduce the level of egg white protein impurities.

Refer to FIG. 4 for a schematic representation of this unit operation.

Precipitation at pH 5.4 and Low pH Incubation for Viral Inactivation

After the phenyl-HIC, the eluate was collected, and the pH was reduced to a pH of 5.4 while mixing the eluate. The pH-adjusted eluate was then subjected to depth filtration and 0.2 μm filter train. The temperature was maintained at 18-25° C. The purpose of the pH 5.4 precipitation step is reduction of EW protein impurities.

Figure 5:
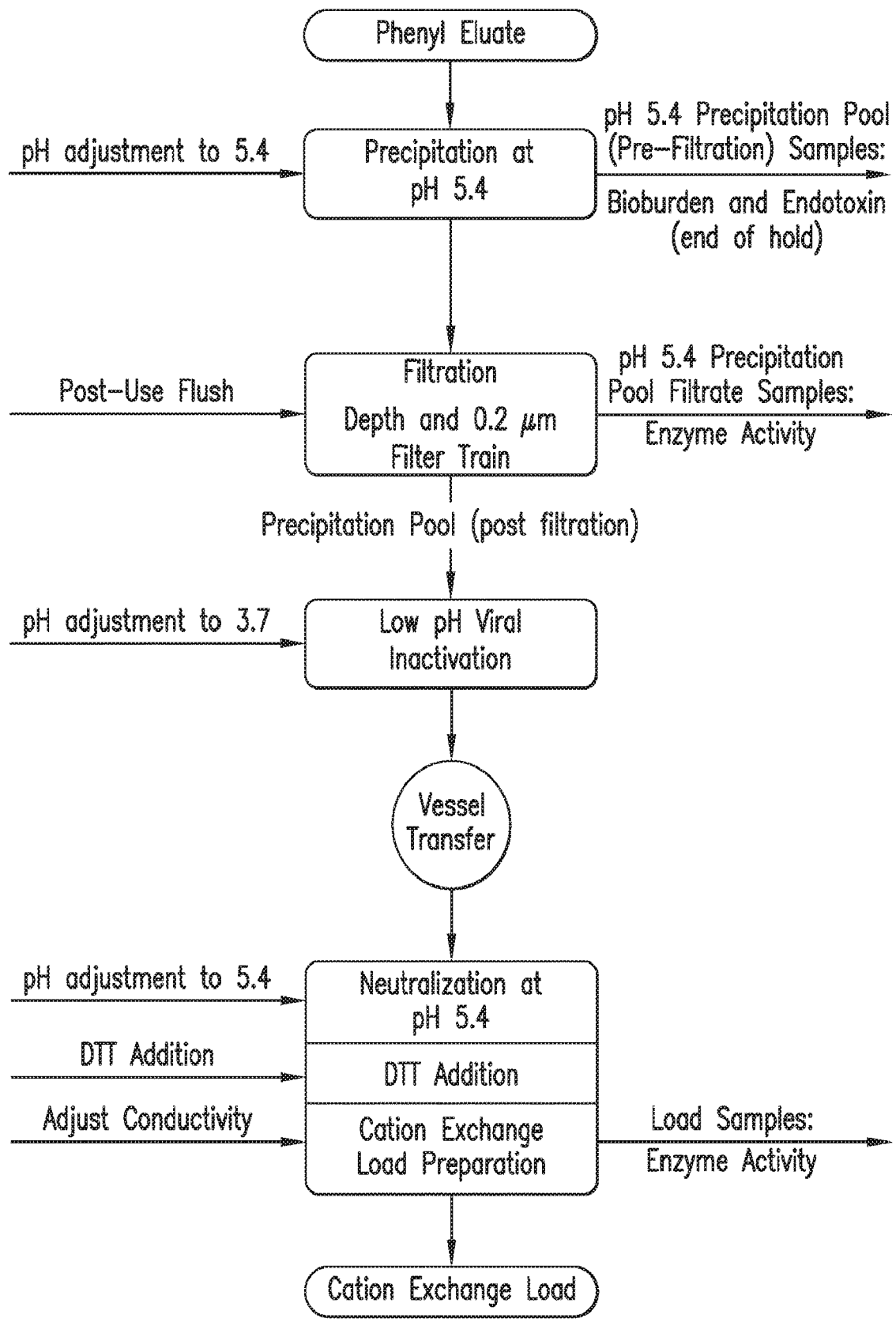
FIG. 5: Schematic representation of the low pH precipitation/filtration and low pH viral inactivation process outlined in Example 1 for semi-processed egg whites.

The pH of the precipitation pool (post filtration) was further lowered to a pH of 3.7 while mixing. The pH was held for 60-90 minutes. The purpose of low pH incubation step is viral inactivation. Refer to FIG. 5 for a schematic representation of this unit operation.

Cation Exchange Chromatography

Figure 6:
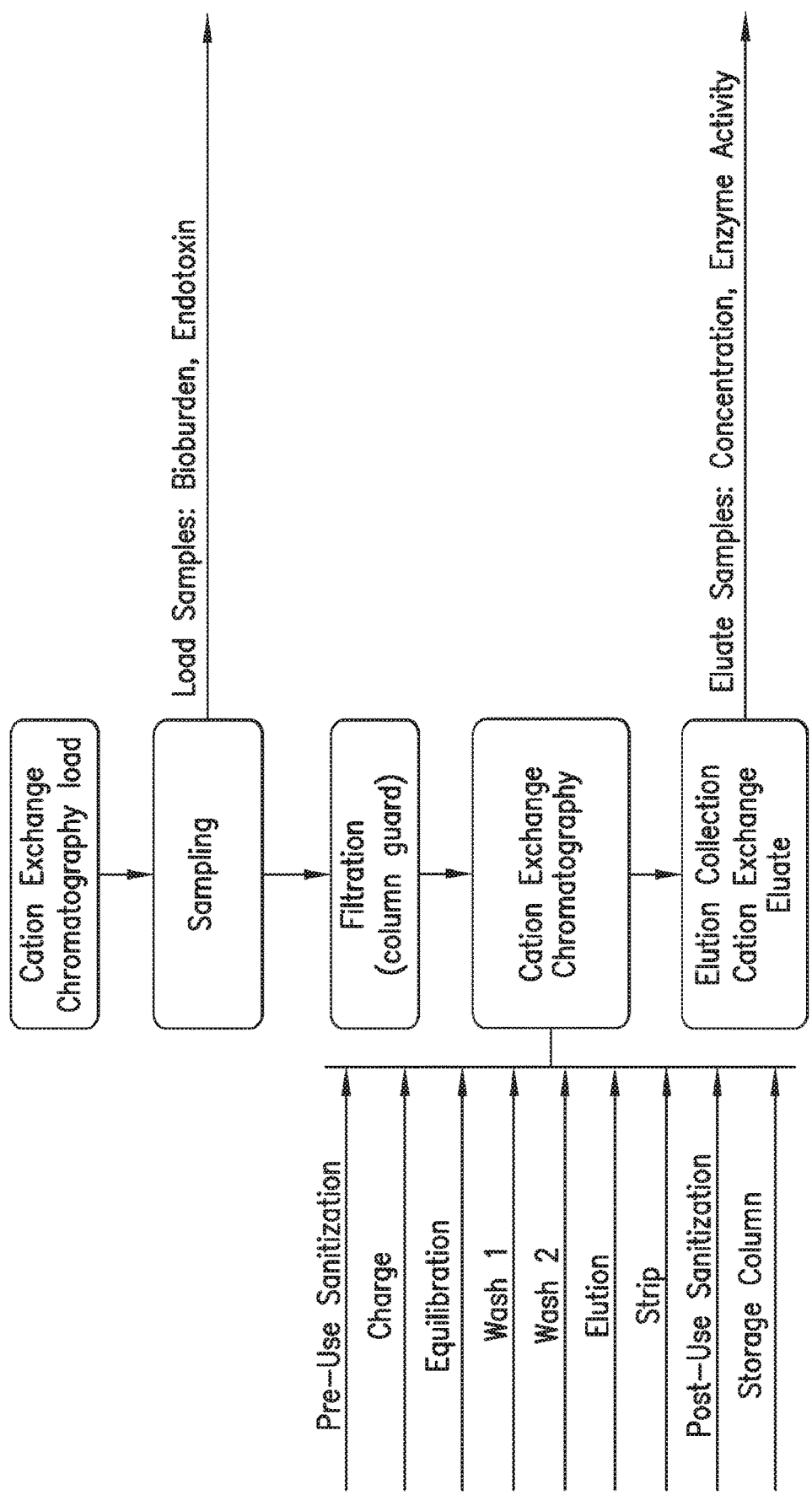
FIG. 6: Schematic representation of the process for cation exchange chromatography in Example 1 to remove protein impurities and as a viral clearance step.

After viral inactivation, the precipitation pool was subjected to cationic exchange chromatography using Toyopearl GigaCap S matrix. The pH of the precipitation pool was raised to 5.7 to 5.9 using Tris and then dithiolthreitol was added. Chromatography proceeded by using a GigaCap S cation exchange column (methyl sulfonate; Tosoh Bioscience LLC, King of Prussia, Pa.). The cation exchange chromatography unit operation reduces EW protein impurities and serves as a viral clearance step. Refer to FIG. 6 for a schematic representation of the cation exchange chromatography step.

Nanofiltration

Figure 7:
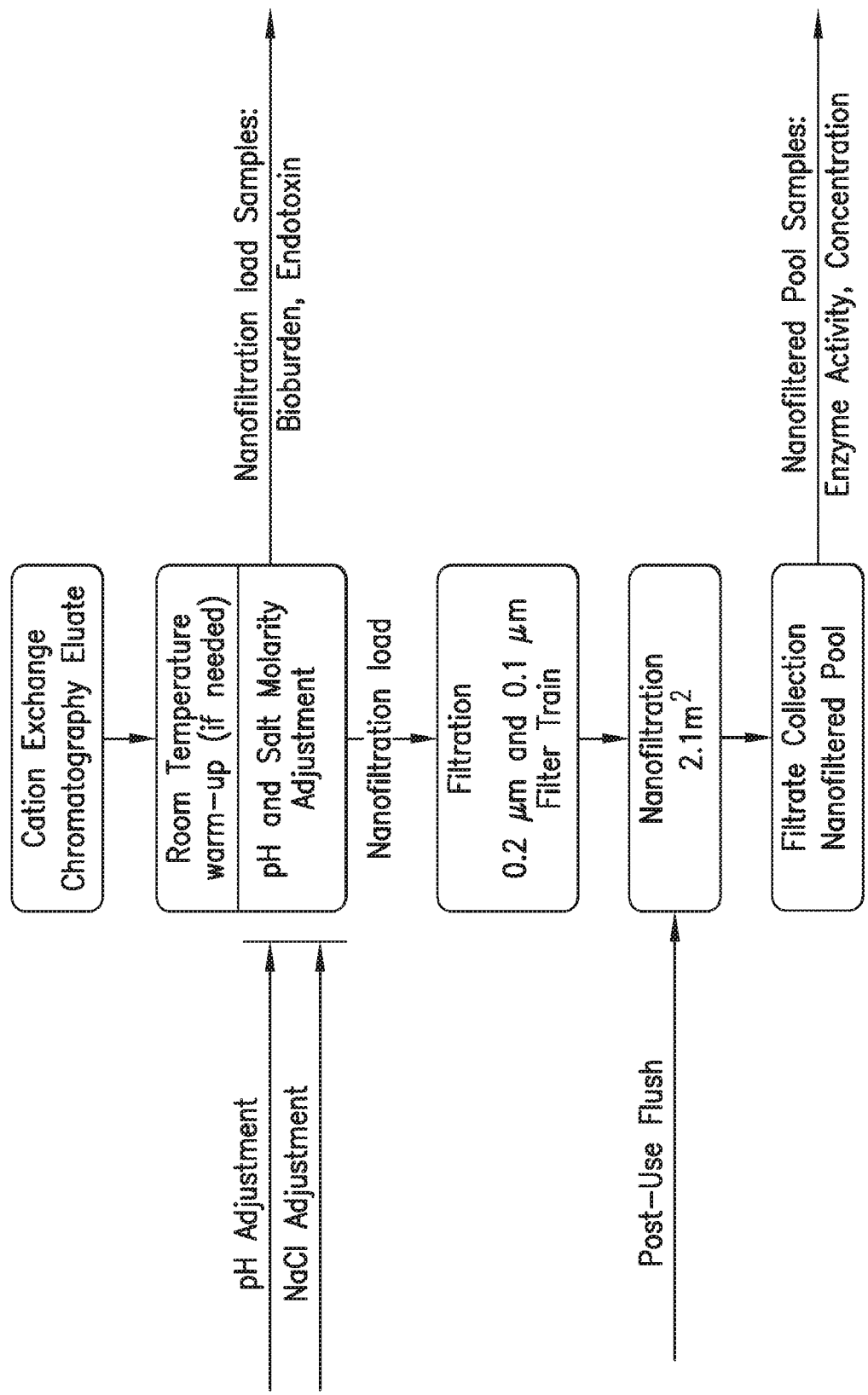
FIG. 7: Schematic representation of the process of nanofiltration of the eluate from the cation exchange chromatography matrix of Example 1, used as a viral clearance step.

The cation exchange chromatography eluate was subjected to nanofiltration to remove potential adventitious viruses from the process stream. The eluate was warmed to room temperature, and the pH and salt molarity was adjusted. The eluate was then subjected first to a 0.2 μm filter, and then a 0.1 μm filter. After washing, the filtrate was then collected. Refer to FIG. 7 for a schematic of the nanofiltration step.

Anion Exchange Membrane Chromatography

Figure 8:
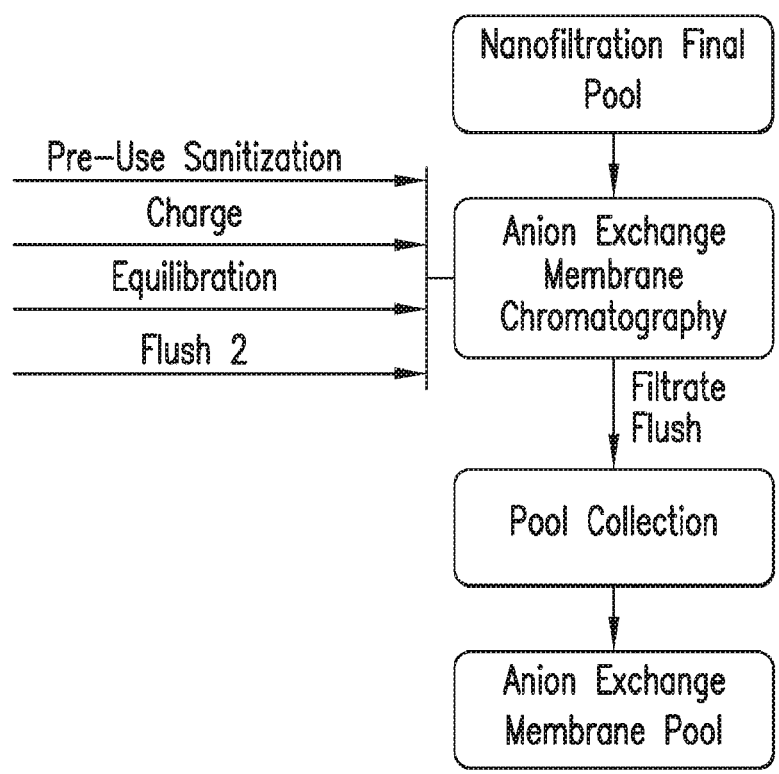
FIG. 8: Schematic representation of anion exchange membrane chromatography of the product from the nanofiltration of Example 1.

After nanofiltration, the filtrate was subjected to anion exchange chromatography using a Mustang Q anionic membrane. The membrane was first equilibrated at pH 6.7-6.9. The anion exchange membrane chromatography step removes potential adventitious agents from the process stream. Refer to FIG. 8 for a schematic of the anion exchange membrane chromatography step.

Butyl Hydrophobic Interaction Chromatography

Figure 9:
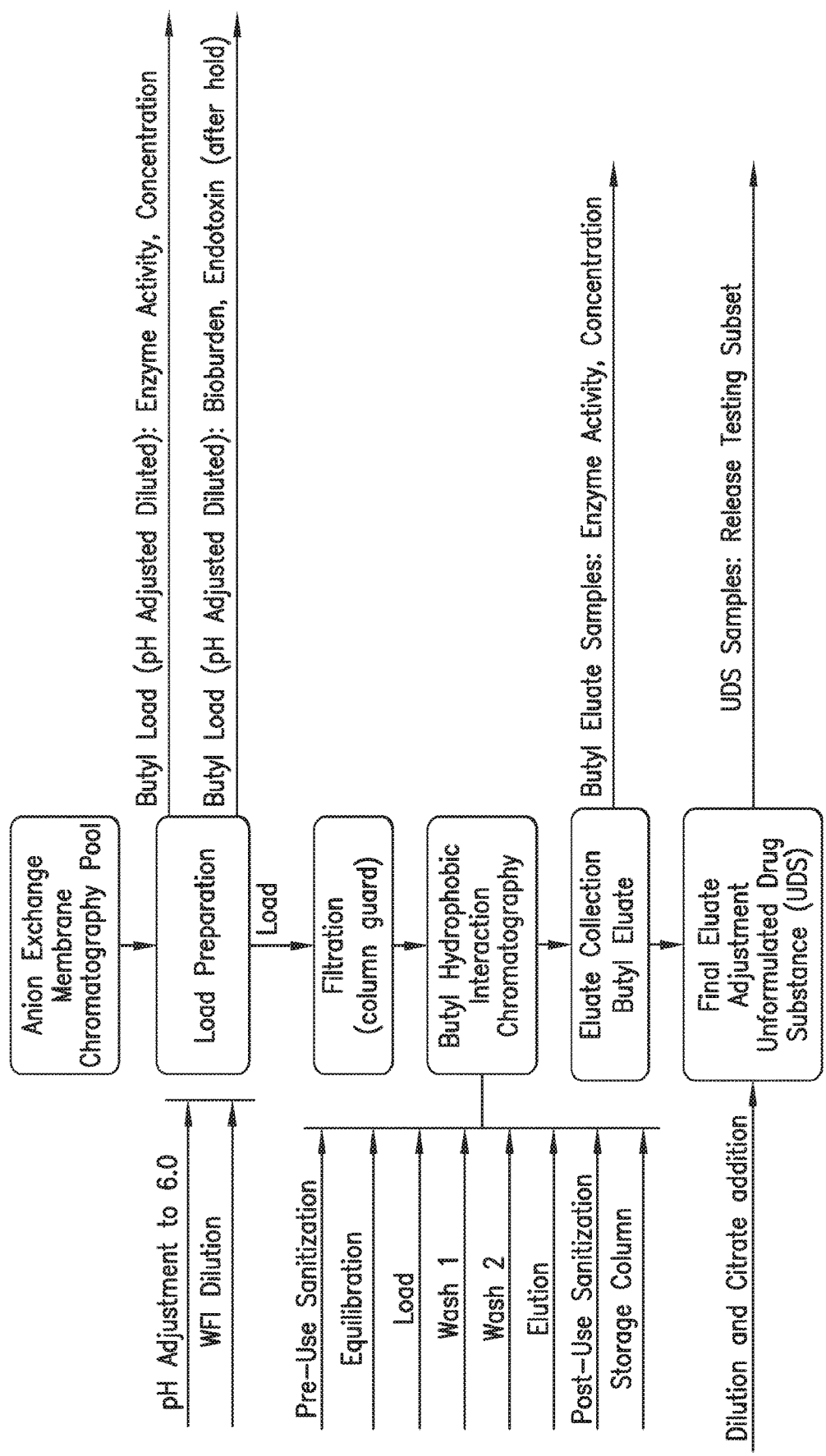
FIG. 9: Schematic representation of butyl hydrophobic interaction chromatography of the product from the anion exchange membrane chromatography process of Example 1, used as a polishing step.

The pool from the anion exchange membrane chromatography was then subjected to butyl hydrophobic interaction chromatography as a final polishing step. The pH of the pool was adjusted to 6.0 (pH below pH 5.9 resulted in poor host protein clearance) at a temperature of 2-8 OC. The butyl-HIC column was equilibrated, and then the pool was loaded onto the column. The column was washed three times, and then the sebelipase alfa product was eluted, and the eluate was collected. FIG. 9 is a schematic of the Butyl-HIC step.

Ultrafiltration/Diafiltration/Diafiltration (UFDF)

Figure 10:
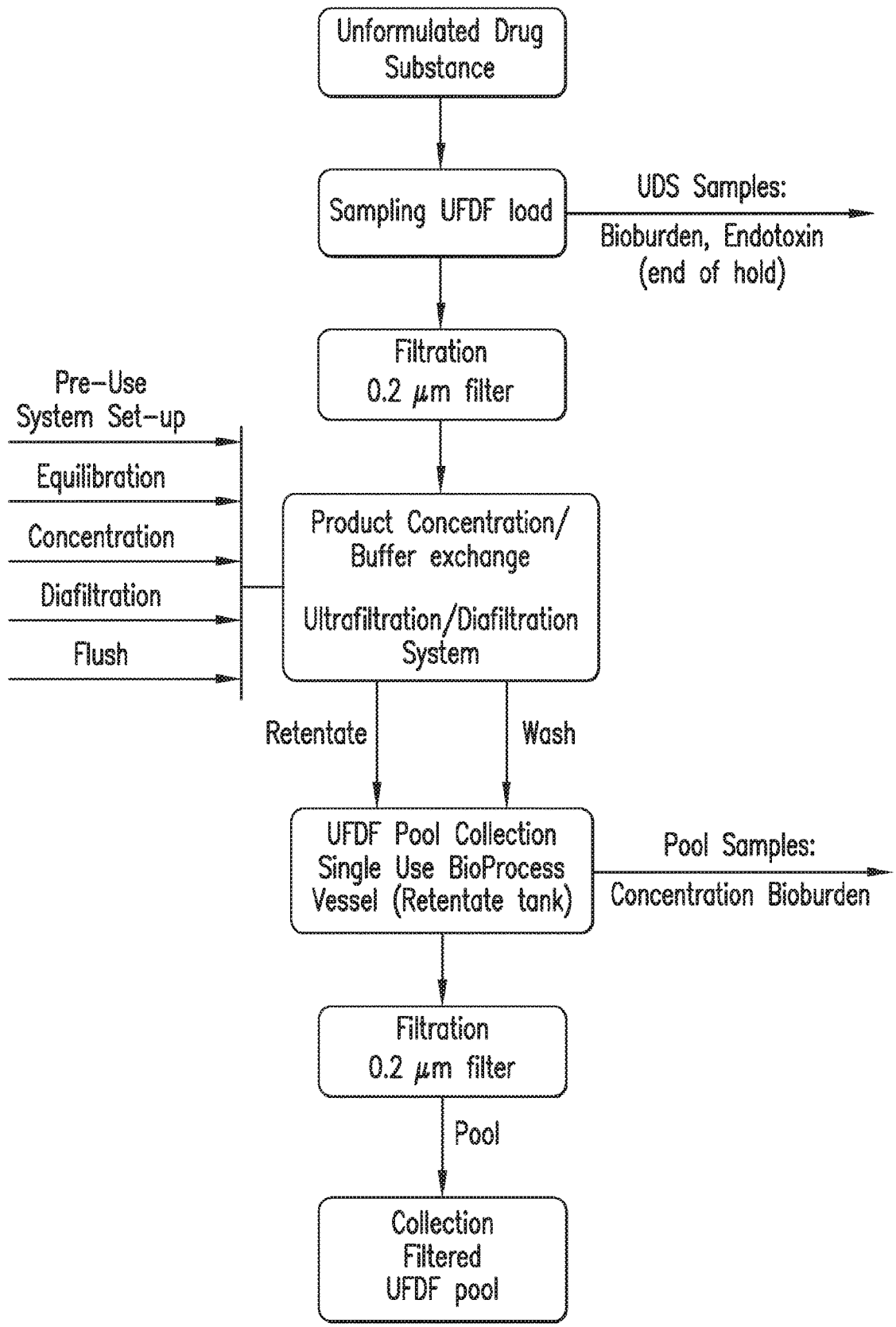
FIG. 10: Schematic representation of ultrafiltration/diafiltration (UF/DF) of the product from the butyl hydrophobic interaction chromatography process, used to concentrate the sebelipase alfa in Example 1.

The eluate from the butyl-HIC column was the subjected to ultrafiltration/diafiltration. The UF/DF was equilibrated, and then sebelipase alfa product was loaded and concentrated. During the UFDF step, sebelipase alfa is concentrated in the presence of Human Serum Albumin (HSA) and the UDS matrix is exchanged to the DS formulation buffer (54 mM Sodium Citrate, pH 5.9). FIG. 10 is a schematic of the UF/DF step.

Formulation and Drug Substance Filling

Figure 11:
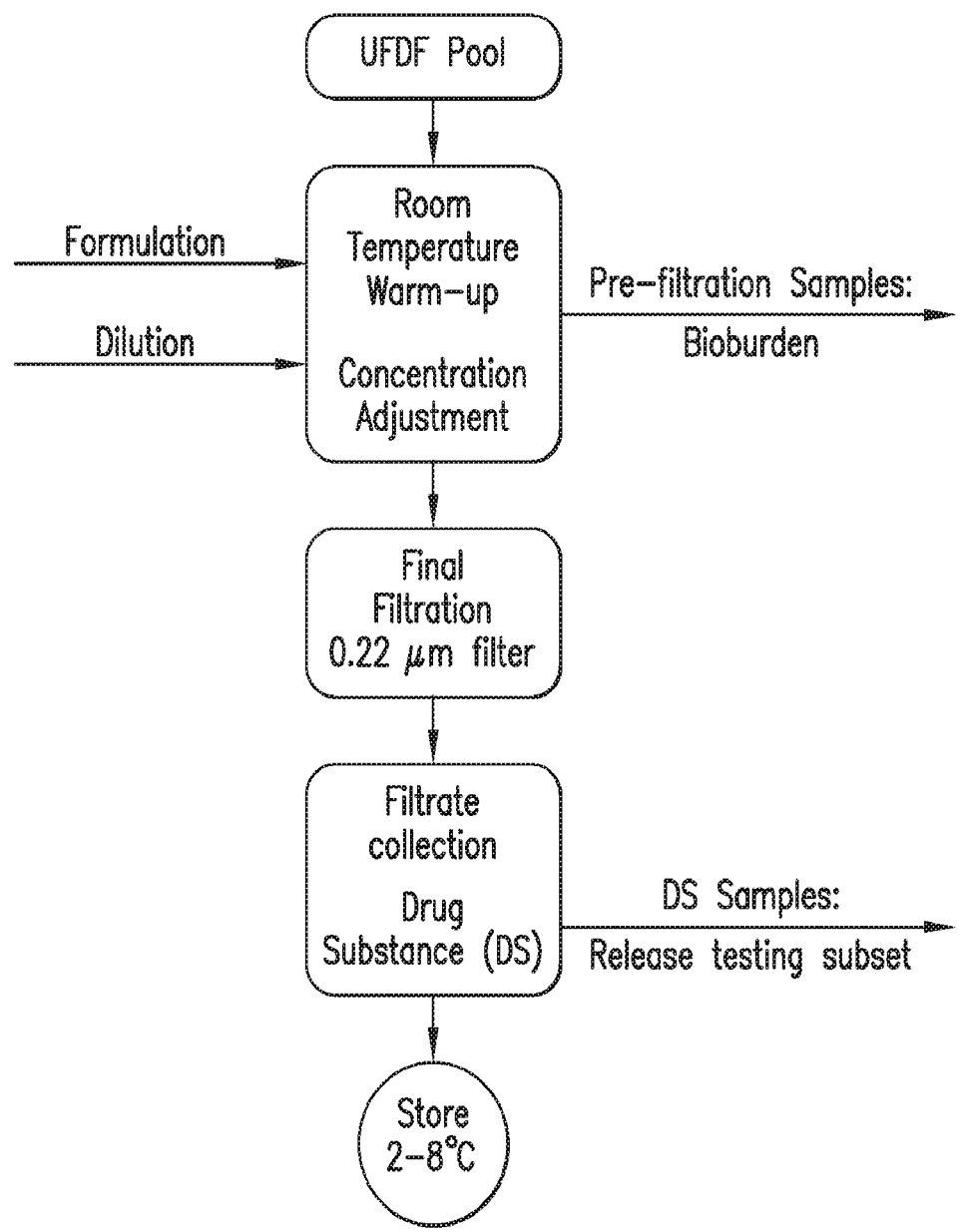
FIG. 11: Schematic representation of formulation and drug substance filling step, to adjust the concentration of the ultrafiltration/diafiltration (UF/DF) product comprising sebelipase alfa from the product resulting from the butyl hydrophobic interaction chromatography process in Example 1.

The purpose of the formulation and Drug Substance filling step is to adjust the UFDF pool to the correct concentrations of sebelipase alfa and HSA and then filter the DS into storage containers. FIG. 11 is a diagram of the Formulation and DS filling step.

Some preferred controls of the sebelipase alfa purification are listed in Table 2.

TABLE 2

Controls in the sebelipase alfa purification process.

| Unit Operation | Testing Point | Parameter | Limits | Rationale |
|---|---|---|---|---|
| Clarification | Clarified EW (PHIC Load) | In vitro cell culture for adventitious agent | Negative | Control of adventitious agent |
| | | Mycoplasma | Negative | Control of adventitious agent |
| | | West Nile PCR | Negative | Control of adventitious agent |
| | | Influenza A PCR | Negative | Control of adventitious agent |
| Precipitation at pH 5.4 and Low pH Viral Inactivation | Low pH viral inactivation (initial) | pH | 3.6-3.8 | Validated process parameter ranges for low pH viral inactivation |
| | Low pH viral inactivation (final) | pH | 3.6-3.8 | |
| | Low pH viral inactivation (final) | Time at pH 3.6 to 3.8 (min) | 60-90 | |
| | Low pH viral inactivation (initial) | Temperature (° C.) | 18-25 | |
| | Low pH viral inactivation (final) | Temperature (° C.) | 18-25 | |
| Cation Exchange Chromatography (Giga Cap S) | Elution Buffer (prior to use) | pH | 5.70-5.90 | pH below 5.70 results in poor product recovery for this unit operation. pH above 5.90 reduces lysozyme and ovotransferrin clearance. |
| | Elution Buffer (prior to use) | Conductivity (mS/cm) | 8.5-10.5 | Functions synergistically with elution pH for product recovery |
| | Eluate Pool | Total sebelipase alfa mass (g) (A280) | ≤124 | This upper limit is the protein load limit validated for viral clearance on the Mustang Q filter. This is based on the 0.52 L Membrane Volume (LMV) filter used in the process. Control at this step allows easier process manipulation since it coincides with a process intermediate hold point. |
| Nanofiltration | Nanofiltration Filtrate | Final quantity (kg) | ≤105 | The upper limit is the total mass of filtrate validated for viral clearance on the nanofilter. This is based on the 2.1 m$^2$ surface area filter used in the process. |
| | Post Use | Filter Integrity Test | Pass | Demonstrates integrity of the filter during operations |
| Unit Operation | Testing Point | Parameter | Limits | Rationale |
| Anion Exchange Chromatography (Mustang Q) | Equilibration Buffer | pH | 6.7-6.9 | Viral clearance was validated with this pH range |
| | | Conductivity (mS/cm) | 11-17 | Viral clearance was validated with this conductivity range |
| | Load | pH | 6.7-6.9 | Viral clearance was validated with this pH range |
| | | Conductivity (mS/cm) | 11-17 | Viral clearance was validated with this conductivity range |
| Butyl HIC Chromatography | Wash 1 Buffer | pH | >5.9 | pH below pH 5.9 resulted in poor host protein clearance |
| | Wash 2 Buffer | pH | >5.9 | pH below pH 5.9 resulted in poor host protein clearance |
| | UDS | Total Protein Concentration by UV absorption (mg/mL) | 0.5-1.5 | This protein concentration is used to calculate normalized values for endotoxin |
| Ultrafiltration/ Diafiltration | Pre-Use | Filter Integrity Test | Pass | Ensures filter is integral prior to operations. |
| | | Water Flux Test (LMH) | ≥4.3 LMH/psi | Ensures that the membrane is fully wetted prior to operations |

TABLE 2-continued

Controls in the sebelipase alfa purification process.

| Unit Operation | Testing Point | Parameter | Limits | Rationale |
|---|---|---|---|---|
| | UF Buffer | pH | 5.8-6.0 | Final formulation buffer |
| | | Conductivity (mS/cm) | 8.5-10.5 | Final formulation buffer |
| | Equilibration | pH | 5.8-6.0 | Ensures sanitisation solution is removed from the system and the membrane is fully equilibrated prior to use |
| | | Conductivity (mS/cm) | 8.5-10.5 | Ensures sanitisation solution is removed from system and membrane fully equilibrated prior to use |
| Formulation and Drug Substance Fill | Drug Substance filtration | Post Use filter integrity test | Pass | Demonstrates bioburden control during DS filling |

The sebelipase alfa process was designed with process hold points to allow for operational flexibility (e.g. to accommodate scheduling, or delays due to equipment readiness) or to await results from in-process control tests. The suitability of process hold points was established during process characterization studies evaluating the stability of sebelipase alfa in different buffer environments. Hold points and hold times were validated at full scale by demonstrating the stability of process intermediates and microbiological control during the hold.

Table 3 lists process intermediate hold time limits and storage conditions reflecting maximum hold durations demonstrated during validation. Process intermediates with storage durations of less than 24 hours are not considered intermediate hold points in the process. The process intermediate hold times are listed in Table 3.

TABLE 3

Process Intermediate Hold Times

| Unit Operation | Hold Point | Hold Time |
|---|---|---|
| Clarification | Egg White Thaw/Pooled Egg White | Time: ≤5 days Temperature: 2-8° C. |
| Clarification | Clarified Egg White/Phenyl-HIC Load | Time: ≤24 hrs Temperature: 2-8° C. |
| Precipitation at pH 5.4 and Low pH Viral Inactivation | pH 5.4 Pool (prior to filtration) | Time: ≤3 days Temperature: 2-8° C. |
| Cation Exchange Chromatography | Eluate | Time: ≤3 days. Temperature: 2-8° C. |
| Butyl-HIC Chromatography | Load | Time: ≤3 days Temperature: 2-8° C. |
| Butyl-HIC Chromatography | Unformulated Drug Substance | Time: ≤7 days Temperature: 2-8° C. |
| Formulation and Drug Substance Fill | Filtered UFDF Pool | Time: ≤3 days Temperature: 2-8° C. |

It will be readily apparent to one of ordinary skill in the relevant arts that other suitable modifications and adaptations to the methods and applications described herein can be made without departing from the scope of any of the embodiments. The following examples are included herewith for purposes of illustration only and are not intended to be limiting.

It is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

While various embodiments have been described above, it should be understood that they have been presented only as illustrations and examples of the present technology, and not by way of limitation. It will be apparent to persons skilled in the relevant art that various changes in form and detail can be made therein without departing from the spirit and scope of the present technology. Thus, the breadth and scope of the present technology should not be limited by any of the above-described embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of purifying a therapeutic heterologous protein from an egg white comprising the therapeutic heterologous protein, the method comprising;
   a. adjusting the pH of the egg white to a pH of 5.8 to 6.5 to form a pH-adjusted egg white;
   b. filtering the pH-adjusted egg white of (a) and collecting a first filtrate;
   c. subjecting the first filtrate of (b) to a hydrophobic interaction chromatography matrix, and collecting a first eluate comprising the therapeutic heterologous protein;
   d. adjusting the pH of the first eluate of (c) to a pH of 5.0 to 5.6 to form a pH-adjusted eluate;
   e. filtering the pH-adjusted eluate to obtain a second filtrate;
   f. adjusting the pH of the second filtrate to a pH of 3.0 to 4.0 to form a pH-adjusted second filtrate;
   g. neutralizing the pH-adjusted second filtrate of (f) to a pH of 5.0 to 8.0 to form a neutralized solution;
   h. subjecting the neutralized solution to a cation exchange chromatography matrix and collecting a second eluate comprising the therapeutic heterologous protein.

2. The method of claim 1, further comprising (i) subjecting the second eluate to nanofiltration to form a third filtrate, and (j) subjecting the third filtrate to an anion exchange chromatography matrix and collecting a third eluate comprising the therapeutic heterologous protein.

3. The method of claim 2, further comprising (k) subjecting the third eluate to a second hydrophobic interaction chromatography matrix, and collecting a fourth eluate comprising the therapeutic heterologous protein.

4. The method of claim 3, further comprising (1) subjecting the fourth eluate to ultrafiltration/diafiltration (UF/DF).

5. The method of claim 1, wherein the therapeutic heterologous protein is sebelipase alfa.

6. The method of claim 1, wherein the egg white is a pooled egg white with a volume of greater than 1 liter.

7. The method of claim 1, wherein the egg white is a pooled egg white with a volume of greater than 10 liters.

8. The method of claim 1, wherein the egg white is a pooled egg white with a volume of greater than 50 liters.

9. The method of claim 1, wherein the pH of (a) is between 5.9 and 6.2.

10. The method of claim 1, wherein the pH of (a) is adjusted using an acidic buffer.

11. The method of claim 1, wherein the pH of (a) or (d) is adjusted using an acidic buffer comprising an acidic agent selected from the group consisting of acetic acid, hydrochloric acid, sulfuric acid, nitric acid, phosphoric acid, hydrofluoric acid, hydrobromic acid, perchloric acid, citric acid, boric acid, tartaric acid, lactic acid, formic acid, oxalic acid, uric acid, and barbituric acid.

12. The method of claim 10, wherein the acidic buffer comprises about 5M to about 6M of an acetate salt.

13. The method of claim 10, wherein the acidic buffer comprises about 5M to about 6M sodium acetate.

14. The method of claim 10, wherein the acidic buffer is from about 0.5 wt % to about 2 wt % per kilogram of the egg white.

15. The method of claim 10, wherein the pH of the acidic buffer is about 4.0 to about 6.5.

16. The method of claim 10, wherein the acidic buffer is added to the egg white of (a) at a rate of at least about 1% (vol/vol) per minute.

17. The method of claim 1, wherein the egg white is stirred concurrently while the pH is adjusted.

18. The method of claim 1, wherein the egg white of (a) is about 2° C. to about 25° C.

19. The method of claim 1, wherein the conductivity of the pH-adjusted egg white is about 8 mS/cm to about 20 mS/cm.

20. The method of claim 1, further comprising:
   (i) allowing the pH-adjusted egg white to settle such that the egg white separates into top, middle and bottom layers, isolating the middle layer, and subjecting the isolated middle layer to the filtering in (b); or
   (ii) centrifuging the pH-adjusted egg white to collect a fraction comprising sebelipase alfa, and then subjecting the fraction comprising sebelipase alfa to the filtering in (b).

21. The method of claim 1, wherein the filtering of (b) comprises passing the pH-adjusted egg white through a filter having an average pore size ranging from about 0.1 μm to about 100 μm.

22. The method of claim 1, wherein the filtering of (b) comprises passing the pH-adjusted egg white through a plurality of filters.

23. The method of claim 21, wherein the filter comprises an area of at least about 2 m².

24. The method of claim 21, wherein the filter comprises an area of at least about 8 m².

25. The method of claim 21, wherein the egg white is passed through the filter under a differential pressure less than about 30 psi.

26. The method of claim 21, wherein the egg white is passed through the filter under a differential pressure less than about 15 psi.

27. The method of claim 1, wherein the first filtrate is warmed to room temperature.

28. The method of claim 1, wherein the hydrophobic interaction chromatography matrix of (c) is a phenyl, octyl, or butyl hydrophobic interaction chromatography matrix.

29. The method of claim 1, wherein the hydrophobic interaction chromatography matrix of (c) is a phenyl hydrophobic interaction chromatography matrix.

30. The method of claim 1, wherein the therapeutic heterologous protein is eluted from the hydrophobic interaction chromatography matrix by a decreasing salt gradient.

31. The method of claim 1, wherein the pH of (d) is adjusted to a pH of 5.2 to 5.5.

32. The method of claim 1, wherein the filtering of (e) comprises passing the eluted therapeutic heterologous protein through a filter having an average pore size ranging from about 0.1 μm to about 10 μm.

33. The method of claim 1, wherein the filtering of (e) comprises passing the eluted therapeutic heterologous protein through a filter having an average pore size ranging from about 0.5 μm to about 5 μm.

34. The method of claim 1, wherein the pH of the second filtrate is adjusted using an acidic buffer comprising an acidic agent selected from the group consisting of acetic acid, hydrochloric acid, sulfuric acid, nitric acid, phosphoric acid, hydrofluoric acid, hydrobromic acid, perchloric acid, citric acid, boric acid, tartaric acid, lactic acid, formic acid, oxalic acid, uric acid, and barbituric acid.

35. The method of claim 1, wherein the pH of the second filtrate is adjusted to a pH of 3.5 to 3.9.

36. The method of claim 1, wherein the pH of the pH-adjusted second filtrate is maintained for 10 minutes to 40 minutes.

37. The method of claim 1, wherein the pH-adjusted second filtrate is neutralized according to (g) using a basic buffer comprising a basic agent selected from the group consisting of an amine, ammonia, a carbonate, a bicarbonate, a borate, and a phosphate.

38. The method of claim 1, wherein the cation exchange chromatography matrix is selected from a matrix comprising a methyl sulfonate group, diethylaminoethyl group or an ammonium group.

39. The method of claim 1, wherein the therapeutic heterologous protein is eluted using an increasing salt gradient.

40. The method of claim 2, wherein the nanofiltration of (i) comprises passing the second eluate through a filter having an average pore size from about 0.05 μm to about 0.2 μm.

41. The method of claim 2, wherein the nanofiltration of (i) comprises passing the second eluate through multiple nanofilters.

42. The method of claim 2, wherein the anion exchange chromatography matrix is selected from a matrix comprising a quaternary ammonium, diethylaminoamonethyl (DEAE) group or diethylaminoethyl group.

43. The method of claim 3, wherein the second hydrophobic interaction chromatography matrix is different from the hydrophobic interaction chromatography matrix of (c).

44. The method of claim 3, wherein the second hydrophobic interaction chromatography matrix is a butyl-hydrophobic interaction chromatography matrix.

45. The method of claim 4, wherein the ultrafiltration/diafiltration comprises passing the third eluate through a filter having an average pore size from about 0.02 μm to about 0.4 μm.

46. The method of claim 4, wherein ultrafiltration/diafiltration results in the concentration of the therapeutic heterologous protein to about 0.5 mg/ml to about 5 mg/ml.

47. The method of claim 4, wherein the ultrafiltration/diafiltration comprises use of a citrate buffer.

* * * * *